(12) United States Patent
Akiba et al.

(10) Patent No.: US 11,672,851 B2
(45) Date of Patent: Jun. 13, 2023

(54) NY-ESO-1-CONTAINING ARTIFICIAL ADJUVANT VECTOR CELL FOR USE IN TREATMENT OF CANCER

(71) Applicants: ASTELLAS PHARMA INC., Tokyo (JP); RIKEN, Saitama (JP)

(72) Inventors: Ayaka Akiba, Tokyo (JP); Tatsuya Okudaira, Tokyo (JP); Yasuhide Masuhara, Tokyo (JP); Keisuke Ohsumi, Tokyo (JP); Shinichiro Fujii, Saitama (JP)

(73) Assignees: RIKEN, Saitama (JP); ASTELLAS PHARMA INC., Tokyo (JP)

(*) Notice: Subject to any disclaimer, the term of this patent is extended or adjusted under 35 U.S.C. 154(b) by 0 days.

(21) Appl. No.: 17/781,616

(22) PCT Filed: Dec. 1, 2020

(86) PCT No.: PCT/JP2020/044586
§ 371 (c)(1),
(2) Date: Jun. 1, 2022

(87) PCT Pub. No.: WO2021/112055
PCT Pub. Date: Jun. 10, 2021

(65) Prior Publication Data
US 2023/0000965 A1 Jan. 5, 2023

(30) Foreign Application Priority Data
Dec. 2, 2019 (JP) .............................. JP2019-217704

(51) Int. Cl.
| | | |
|---|---|---|
| A61K 39/00 | (2006.01) | |
| C07K 14/74 | (2006.01) | |
| C07K 14/705 | (2006.01) | |
| C12N 5/10 | (2006.01) | |
| C12N 5/071 | (2010.01) | |
| A61K 35/00 | (2006.01) | |
| A61P 35/00 | (2006.01) | |
| A61K 45/06 | (2006.01) | |

(52) U.S. Cl.
CPC ...... *A61K 39/001188* (2018.08); *A61K 45/06* (2013.01); *A61P 35/00* (2018.01); *C07K 14/705* (2013.01); *C07K 14/70539* (2013.01); *C12N 5/0686* (2013.01); *C12N 5/10* (2013.01); *A61K 2039/5156* (2013.01); *C12N 2510/00* (2013.01)

(58) Field of Classification Search
CPC .................. C12N 5/10; C12N 2510/00; A61K 2039/5156; A61K 39/001188; A61P 35/00; C07K 14/705; C07K 14/70539
See application file for complete search history.

(56) References Cited

U.S. PATENT DOCUMENTS

| | | | | |
|---|---|---|---|---|
| 9,783,821 | B2* | 10/2017 | Fujii | ...................... C07K 14/82 |
| 10,316,332 | B2* | 6/2019 | Fujii | ............ A61K 39/001153 |
| 11,072,802 | B2* | 7/2021 | Fujii | .................. C07K 14/4748 |
| 2008/0254045 | A1* | 10/2008 | Donda | .................... A61P 31/04 |
| | | | | 435/375 |
| 2009/0304736 | A1* | 12/2009 | Yang | ....................... A61P 37/04 |
| | | | | 435/243 |
| 2010/0233215 | A1 | 9/2010 | Fujii et al. | |
| 2011/0280895 | A1 | 11/2011 | Fujii et al. | |
| 2013/0189302 | A1* | 7/2013 | Fujii | ..................... C12N 15/85 |
| | | | | 435/375 |
| 2014/0179004 | A1 | 6/2014 | Fujii et al. | |
| 2017/0216370 | A1 | 8/2017 | Falb et al. | |

FOREIGN PATENT DOCUMENTS

| | | |
|---|---|---|
| JP | 2018-521674 A | 8/2018 |
| WO | WO-2007/097370 A1 | 8/2007 |
| WO | WO-2010/061930 A1 | 6/2010 |
| WO | WO-2013/018778 A1 | 2/2013 |
| WO | WO-2017/023818 A1 | 2/2017 |

OTHER PUBLICATIONS

University of Iowa Carver College of Medicine, Lentiviral Vectors: Storage and Transduction Instructions, two pages. (Year: 2014).*
Elegheert et al., Nat Protoc. 2018, 13(12):2991-3017.*
Kallunki et al., Cells, 2019, 8, 796, pp. 1-16.*
Ramachandran et al., Seminars in Cancer Biology, 2017, 45:23-35.*
Gasser et al., "A phase I vaccination study with dendritic cells loaded with NY-ESO-1 and alpha-galactosylceramide: induction of polyfunctional T cells in high-risk melanoma patients," Cancer Immunology, Immunotherapy, 2018 (online Nov. 1, 2017), 67(2):285-298.
International Search Report dated Jan. 26, 2021, in PCT/JP2020/044586.
Mahipal et al., "First-in-human phase 1 dose-escalating trial of G305 in patients with advanced solid tumors expressing NY-ESO-1," Cancer Immunology, Immunotherapy, May 8, 2019, 68:1211-1222.
Robbins et al., "A pilot trial using lymphocytes genetically engineered with an NY-ESO-1-reactive T cell receptor: Long term follow up and correlates with response," Clin. Cancer Res., Mar. 1, 2015 (online Dec. 23, 2014), 21(5):1019-1027.
Shimizu et al., "Systemic DC Activation Modulates the Tumor Microenvironment and Shapes the Long-Lived Tumor-Specific Memory Mediated by CD8 T Cells," Cancer Research, Jul. 1, 2016, 76(13):3756-3766.

(Continued)

Primary Examiner — Hong Sang
(74) Attorney, Agent, or Firm — Foley & Lardner LLP

(57) ABSTRACT

An object of the present invention is to provide clinically applicable aAVC-NY-ESO-1 cells stably expressing NY-ESO-1 in order to use aAVC-NY-ESO-1 cells in treating patients having a NY-ESO-1-expressing cancer. The present invention provides, for example, a human-derived cell comprising a polynucleotide encoding CD1d and a polynucleotide encoding NY-ESO-1 or a fragment thereof, wherein the polynucleotide encoding NY-ESO-1 or a fragment thereof is operably linked to an inducible promoter.

4 Claims, 8 Drawing Sheets
Specification includes a Sequence Listing.

(56) References Cited

OTHER PUBLICATIONS

Shimizu et al., "Vaccination with Antigen-Transfected, NKT Cell Ligand-Loaded, Human Cell Elicits Robust In Situ Immune Responses by Dendritic Cells," Cancer Research, Jan. 1, 2013, 73(1):62-73.
Shirahata et al., "Development of versatile high-expression animal host cell/vector system," Lecture Abstracts of Conference of Japan Society of Bioscience and Agrochemistry, 2000, No. 74 Special extra edition, 469, SB-2p-3, with English translation.
Thomas et al., "NY-ESO-1 Based Immunotherapy of Cancer: Current Perspectives," Frontiers in Immunology, May 1, 2018, 9(947):1-14.
Office Action dated Nov. 14, 2021 in EA 202291546, with English translation.

* cited by examiner

The number of days after aAVC(3T3)-NY-ESO-1 administration

NY ESO-1 expression level [ng/10^6 cells]

NY-ESO-1 positive rate [%]

The number of culture days after infection

The number of culture days after infection

FIG. 3

| Promoter | No. | NY-ESO1 expression level [ng/10⁶ cells] | Promoter | No. | NY-ESO1 expression level [ng/10⁶ cells] |
|---|---|---|---|---|---|
| CMV | #01 | 68 | Tet-on | #01 | 331 |
| | #02 | 74 | | #02 | 106 |
| | #03 | 25 | | #03 | 772 |
| | #04 | 12 | | #04 | 308 |
| | #05 | 11 | | #05 | 2503 |
| | #06 | 10 | | #06 | 2573 |
| | #07 | 26 | | #07 | 111 |
| | #08 | 15 | | #08 | 7813 |
| | #09 | 45 | | #09 | 7324 |
| | #10 | 23 | | #10 | 7281 |
| | #11 | 18 | | #11 | 17021 |
| | #12 | 42 | | #12 | 710 |
| | #13 | 10 | | #13 | 1094 |
| | #14 | 15 | | #14 | 32 |
| | #15 | 47 | | #15 | 19413 |
| | #16 | 88 | | #16 | 43890 |
| | #17 | 49 | | #17 | 1519 |
| | | | | #18 | 17720 |
| | | | | #19 | 114 |
| | | | | #20 | 42 |
| | | | | #21 | 3460 |
| | | | | #22 | 629 |
| | | | | #23 | 16 |
| | | | | #24 | 5 |
| | | | | #25 | 844 |
| | | | | #26 | 1566 |
| | | | | #27 | 29514 |
| | | | | #28 | 12313 |
| | | | | #29 | 995 |
| | | | | #30 | 33557 |
| | | | | #31 | 34079 |
| | | | | #32 | 29538 |
| | | | | #33 | 30602 |
| | | | | #34 | 6495 |
| | | | | #35 | 232 |
| | | | | #36 | 295 |
| | | | | #37 | 340 |
| | | | | #38 | 291 |
| | | | | #39 | 2550 |
| | | | | #40 | 747 |
| | | | | #41 | 2397 |
| | | | | #42 | 1814 |
| | | | | #43 | 683 |

NY-ESO-1-CONTAINING ARTIFICIAL ADJUVANT VECTOR CELL FOR USE IN TREATMENT OF CANCER

CROSS-REFERENCE TO RELATED APPLICATIONS

This application is the U.S. National Stage of PCT/JP2020/044586, filed Dec. 1, 2020, which claims priority to JP 2019-217704, filed Dec. 2, 2019.

The instant application contains a Sequence Listing which has been submitted in ASCII format via EFS-WEB and is hereby incorporated by reference in its entirety. Said ASCII copy, created on May 17, 2022, is named sequence.txt and is 29,238 bytes.

TECHNICAL FIELD

The present invention relates to a NY-ESO-1-containing artificial adjuvant vector cell (aAVC-NY-ESO-1 cell) for use in treating a cancer.

BACKGROUND ART

New York esophageal squamous cell carcinoma 1 (NY-ESO-1), one of the cancer/testis antigens, is found to be expressed in a wide range of tumors such as prostate cancer and bladder cancer. On the other hand, its expression is not seen in normal cells of human adults except for the testis. Therefore, this antigen is considered as a suitable target molecule for cancer therapy, and drugs including vaccines are under development (Non Patent Literatures 1 to 3).

A vaccine G305, which is a mixture of the NY-ESO-1 protein and a glucopyranosyl lipid (GLA) adjuvant, is under clinical trial targeting patients having a NY-ESO-1-expressing cancer, and the induction of NY-ESO-1-specific T cells after vaccination has been confirmed (Non Patent Literature 4).

Fujii et al. have prepared an artificial adjuvant vector cell (aAVC) by modifying human-derived cells to exogenously express CD1d and a cancer antigen, and further pulsing the cells with α-galactosylceramide (α-GalCer) (Patent Literatures 1 to 3). This aAVC activates natural killer T (NKT) cells via its CD1d/α-GalCer complex, and the activated NKT cells produce cytokines such as interferon γ (IFN-γ), which in turn activates natural killer (NK) cells or the like. In mouse models, the administration of aAVC has been shown to have a NK cell-dependent antitumor effect (Patent Literatures 1 to 3). aAVC administered to a mouse is immediately killed by activated NKT cells in vivo, and the fragments of the aAVC are taken up into dendritic cells. The dendritic cells taking up the aAVC fragments present a fragment of the cancer antigen with major histocompatibility complex (MHC) on the cell surface, and induce cancer antigen-specific T cells. In mouse models, the administration of aAVC has been shown to have an antitumor effect via the induction of cancer antigen-specific T cells (Patent Literatures 1 to 3 and Non Patent Literatures 5 and 6). Thus, aAVC has been shown to be capable of strongly inducing two immune mechanisms, i.e., innate immunity activation shown by NK cell activation mediated by NKT cell activation and induction of adaptive immunity shown by induction of cancer antigen-specific T cells.

CITATION LIST

Patent Literature

[Patent Literature 1] International Publication No. WO 2007/097370
[Patent Literature 2] International Publication No. WO 2010/061930
[Patent Literature 3] International Publication No. WO 2013/018778

Non Patent Literature

[Non Patent Literature 1] Thomas R. et al., "Frontiers in Immunology", (Switzerland), 2018; 9: 947
[Non Patent Literature 2] Gasser O. et al., "Cancer Immunology, Immunotherapy", (Germany), 2018; 67 (2): 285-298
[Non Patent Literature 3] Robbins P. F. et al., "Clinical Cancer Research", (USA), 2015; 21 (5): 1019-1027
[Non Patent Literature 4] Mahipal A. et al., "Cancer Immunology, Immunotherapy", (Germany), 2019; 68 (7): 1211-1222
[Non Patent Literature 5] Shimizu K. et al., "Cancer Research", (USA), 2013; 73 (1): 62-73
[Non Patent Literature 6] Shimizu K. et al., "Cancer Research", (USA), 2016; 76 (13): 3756-3766

SUMMARY OF INVENTION

Technical Problem

An object of the present invention is to provide aAVC stably expressing NY-ESO-1 or a fragment thereof.

Solution to Problem

The present inventors have conducted considerable diligent studies on the preparation of aAVC expressing NY-ESO-1 as a cancer antigen, and as a result, successfully obtained aAVC stably expressing NY-ESO-1. Specifically, the present inventors have found a problem of constitutively expressed NY-ESO-1, which is reduction in expression level and positive rate with increase in the number of culture days, and solved the problem by diligent studies. Specifically, the present inventors have found that cells inducibly expressing NY-ESO-1 with an inducible promoter (particularly, a drug inducible promoter) show a higher expression level of NY-ESO-1 than in the case of constitutively expressing NY-ESO-1, and successfully obtained aAVC with stably and highly expressing NY-ESO-1 under the control of an inducible promoter (Example 2-2). Specifically, the present invention provides aAVC that can be used for treating a cancer, a method for producing the aAVC, a pharmaceutical composition comprising the aAVC, a method for treating a cancer with the aAVC, etc.

Specifically, the present invention may include the following aspects as a medically or industrially useful substance or method.

[1] A human-derived cell, comprising a polynucleotide encoding CD1d and a polynucleotide encoding NY-ESO-1 or a fragment thereof, wherein the polynucleotide encoding NY-ESO-1 or a fragment thereof is operably linked to an inducible promoter.

[2] The cell according to [1], wherein the NY-ESO-1 is human NY-ESO-1. [3] The cell according to [1] or [2], wherein the CD1d is human CD1d.

[4] The cell according to any one of [1] to [3], wherein the inducible promoter is a drug inducible promoter.

[5] The cell according to [4], wherein the drug inducible promoter is a tetracycline inducible promoter.

[6] The cell according to [5], wherein the tetracycline inducible promoter is TRE3G promoter.

[7] The cell according to any one of [1] to [6], wherein the human-derived cell is a normal cell.

[8] The cell according to [7], wherein the human-derived cell is a cell derived from a human embryonic kidney cell 293 (HEK293) cell.

[9] The cell according to any one of [1] to [8], expressing CD1d and NY-ESO-1 or a fragment thereof.

[10] The cell according to [9], wherein an expression level of the NY-ESO-1 or the fragment thereof is 245 ng to 45000 ng per $10^6$ cells.

[11] The cell according to [9] or [10], wherein a CD1d ligand is loaded on the surface of the cell.

[12] The cell according to [11], wherein the CD1d ligand is α-GalCer.

[13] A pharmaceutical composition comprising a cell according to [11] or [12].

[14] The pharmaceutical composition according to [13] for use in treating a cancer.

[15] A method for treating a cancer, comprising the step of administering a cell according to [11] or [12] to a subject.

[16] The cell according to [11] or [12] for treating a cancer.

[17] Use of a cell according to [11] or [12] for producing a pharmaceutical composition for use in treating a cancer.

[18] A method for producing a cell for use in treating a cancer, comprising the step of culturing a cell according to any one of [1] to [8] in the presence of an inducer of the inducible promoter, thereby inducing the expression of NY-ESO-1 or a fragment thereof.

[19] The method according to [18], further comprising the step of loading α-GalCer onto the surface of the cell.

[20] A method for producing a cell for use in treating a cancer, comprising the step of:
introducing a polynucleotide encoding CD1d and a polynucleotide encoding NY-ESO-1 or a fragment thereof to a human-derived cell, wherein the polynucleotide encoding NY-ESO-1 or a fragment thereof is operably linked to an inducible promoter; or
introducing a polynucleotide encoding NY-ESO-1 or a fragment thereof to a human-derived cell endogenously expressing CD1d, wherein the polynucleotide encoding NY-ESO-1 or a fragment thereof is operably linked to an inducible promoter.

[21] The method according to [20], further comprising the step of culturing the cell obtained in the step in the presence of an inducer of the inducible promoter, thereby inducing the expression of NY-ESO-1 or a fragment thereof.

[22] The method according to [21], further comprising the step of loading α-GalCer on the surface of the cell.

[23] A method for treating a cancer, comprising the step of administering a cell according to [11] or [12] and an immune checkpoint inhibitor to a subject.

[24] The method according to [23], wherein the immune checkpoint inhibitor is a PD-1 immune checkpoint inhibitor or a CTLA-4 immune checkpoint inhibitor.

[25] A method for producing a pharmaceutical composition for use in treating a cancer, comprising the steps of:
thawing a frozen product comprising a cloned human-derived cell comprising a polynucleotide encoding CD1d and a polynucleotide encoding NY-ESO-1 or a fragment thereof, wherein the polynucleotide encoding NY-ESO-1 or a fragment thereof is operably linked to an inducible promoter;
propagating the human cell contained in the frozen product to induce the expression of the NY-ESO-1 or the fragment thereof; and
loading α-GalCer on the surface of the cell.

The aAVC-NY-ESO-1 cell of the present invention and the pharmaceutical composition of the present invention can be used in treating a cancer.

BRIEF DESCRIPTION OF THE DRAWINGS

FIG. 1-2 shows the antitumor effect of aAVC(3T3)-NY-ESO-1 cells in NY-ESO-1-expressing B16 cancer-bearing mice and B16-F10 cancer-bearing mice. The ordinate depicts a tumor volume, and the abscissa depicts the number of days after cancer cell inoculation. The vertical lines depict mean±standard error of the mean, and the number of mice at the time of measurement is shown within the parentheses. A significance probability P value (**: P<0.01) was calculated by comparing the tumor volume on day 20 between a vehicle administration group and an aAVC(3T3)-NY-ESO-1 cell administration group by Student's t-test;

FIG. 1-3 shows the antitumor effect of aAVC(3T3)-NY-ESO-1 cells in NY-ESO-1-expressing B16 cancer-bearing mice. The ordinate depicts a tumor volume, and the abscissa depicts the number of days after aAVC(3T3)-NY-ESO-1 cell inoculation. The vertical lines depict mean±standard error of the mean. A significance probability P value (**: P<0.01) was calculated by comparing the tumor volume on day 10 between a vehicle administration group and an aAVC(3T3)-NY-ESO-1 cell administration group by Dunnett's multiple comparison test;

FIGS. 2-1 to 2-4 show time-dependent change in various indexes of a FreeStyle 293F_CMV_NY-ESO-1_CD1d cell pool (CMV in the drawing) and a FreeStyle 293F_Tet-on_NY-ESO-1_CD1d cell pool (Tet-on in the drawing). FIG. 2-1 shows NY-ESO-1 expression levels per $1\times10^6$ cells of CMV and Tet-on. The ordinate depicts the expression level of NY-ESO-1, and the abscissa depicts the number of culture days after infection;

FIG. 2-2 shows NY-ESO-1 positive rates of CMV and Tet-on. The ordinate depicts the NY-ESO-1 positive rate, and the abscissa depicts the number of culture days after infection;

FIG. 2-3 shows survival rates of CMV and Tet-on. The ordinate depicts the cell survival rate of each pool, and the abscissa depicts the number of culture days after infection;

FIG. 2-4 shows cell doubling times of CMV and Tet-on. The ordinate depicts the doubling time, and the abscissa depicts the number of culture days after infection;

FIG. 3 shows NY-ESO-1 expression levels in various clones isolated from a FreeStyle 293F_CMV_NY-ESO-1_CD1d cell pool (CMV in the drawing) and a FreeStyle 293F_Tet-on_NY-ESO-1_CD1d cell pool (Tet-on in the drawing). No. represents clone numbers, and the numeric values depict NY-ESO-1 expression levels per $1 \times 10^6$ cells;

FIG. 4-1 shows the antitumor effects of aAVC(3T3)-NY-ESO-1 cells, an anti-PD-1 antibody and combined use thereof in NY-ESO-1-expressing B16 cancer-bearing mice. The ordinate depicts a tumor volume, and the abscissa depicts the number of days after aAVC(3T3)-NY-ESO-1 cell administration. The vertical lines depict mean±standard error of the mean, and the number of mice at the time of measurement is shown within the parentheses;

FIG. 4-2 shows the antitumor effects of aAVC(3T3)-NY-ESO-1 cells, an anti-PD-1 antibody and combined use thereof in NY-ESO-1-expressing CT26 cancer-bearing mice. The ordinate depicts a tumor volume, and the abscissa depicts the number of days after aAVC(3T3)-NY-ESO-1 cell administration. The vertical lines depict mean±standard error.

DETAILED DESCRIPTION OF THE PREFERRED EMBODIMENTS

Figure 1:
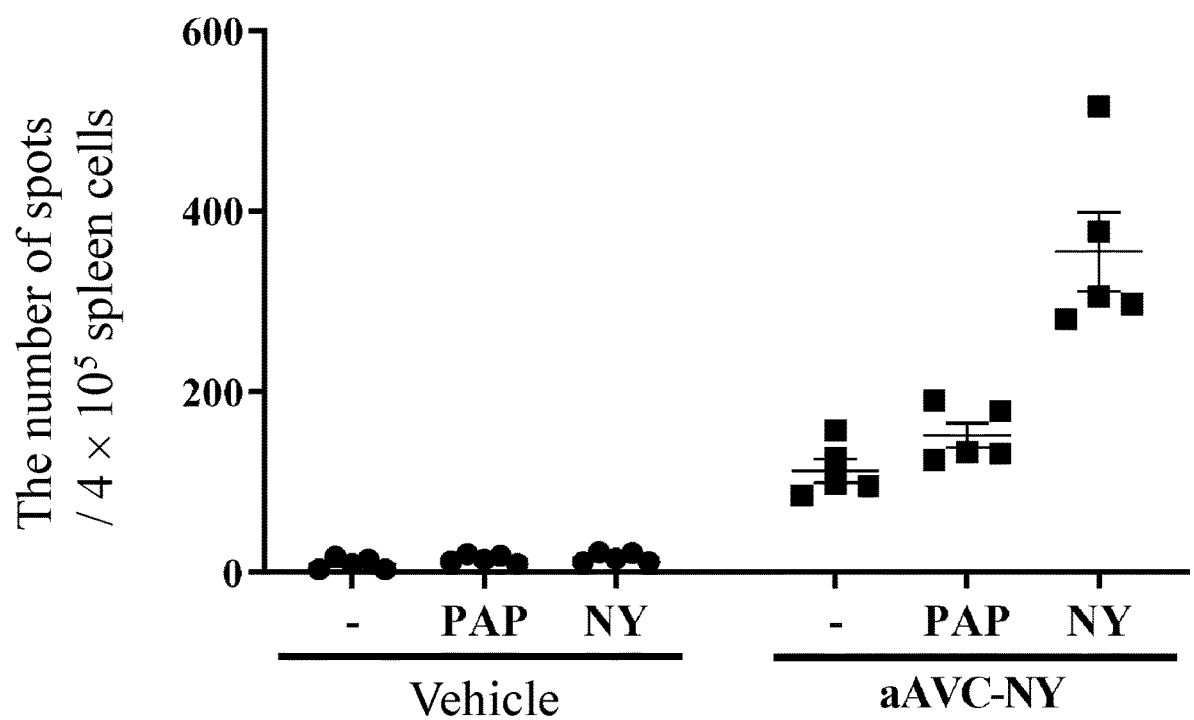
FIG. 1-1 shows the antigen-specific T cell inducing effect of aAVC(3T3)-NY-ESO-1 cells in terms of the number of NY-ESO-1-specific T cells in mice given the aAVC(3T3)-NY-ESO-1 cells. The ordinate depicts the number of spots in $4\times10^5$ spleen cells counted with ELISPOT Reader. In the abscissa, Vehicle depicts a BINACATE administered control group, and aAVC-NY depicts an aAVC(3T3)-NY-ESO-1 administration group. PAP and NY represent PAP peptide and NY-ESO-1 peptide, respectively, used in stimulation. "-" depicts no addition of the peptide. The number of spots per individual and mean±standard error of the mean of the number of spots are shown.
Figure 1:
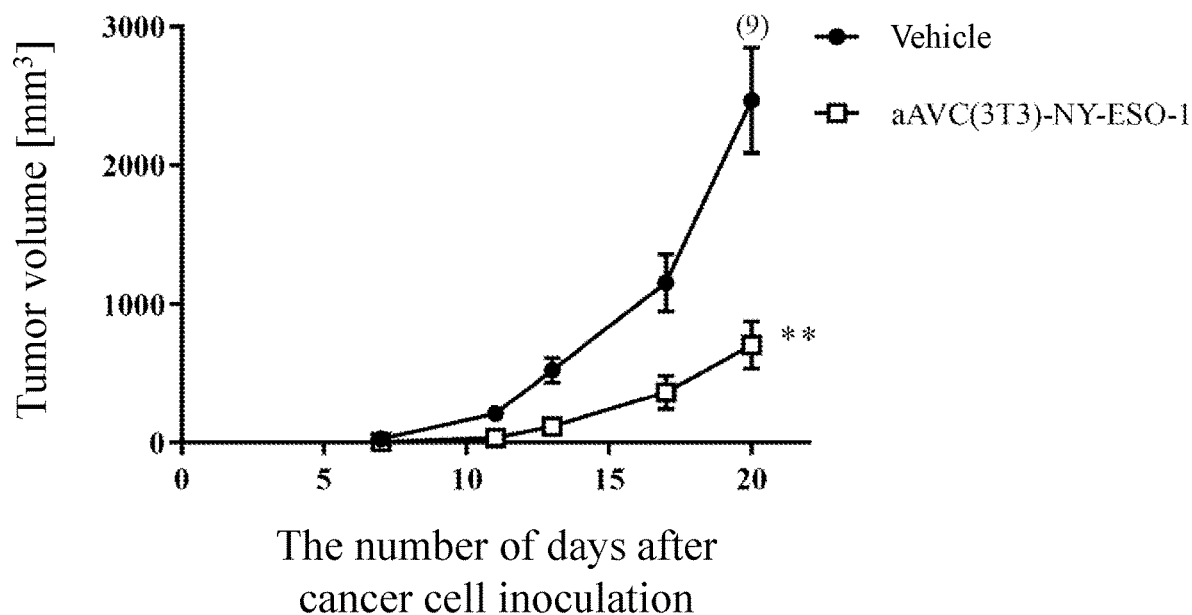

Hereinafter, the present invention will be described in detail. However, the present invention is not limited by detailed description below. Scientific terms and technical terms used in relation to the present invention have meanings generally understood by those skilled in the art, unless otherwise specified herein.

<Artificial Adjuvant Vector Cell>

In the present specification, the terms "artificial adjuvant vector cell" and "aAVC" have the same meaning and are used interchangeably. The terms mean a cell comprising a polynucleotide encoding CD1d polypeptide (hereinafter, also referred to as "CD1d") and polynucleotide(s) encoding one or two or more arbitrary cancer antigens or fragments thereof.

In the present specification, the phrase "comprising a polynucleotide" refers to a state in which a cell endogenously has the polypeptide, or the polynucleotide has been introduced to a cell by an exogenous method. In this context, the term "endogenous" or "endogenously" may be used in a meaning usually used by those skilled in the art in such a way that an isolated cell comprises a particular gene or polynucleotide or expresses a protein. The terms "exogenous" or "exogenously" are used interchangeably so as to refer to introduction of an artificially prepared gene or polynucleotide into a cell of interest by an operation such as gene manipulation or gene introduction, and artificial expression of a protein encoded by the gene or the polynucleotide artificially introduced into the cell of interest.

<AAVC-NY-ESO-1 Cell of Present Invention>

The present invention provides
a human-derived cell comprising
a polynucleotide encoding CD1d, and
a polynucleotide encoding NY-ESO-1 or a fragment thereof, wherein the polynucleotide encoding NY-ESO-1 or a fragment thereof is operably linked to an inducible promoter
(in the present specification, also referred to as an "aAVC-NY-ESO-1 cell").

1. Human-Derived Cell

The human-derived cell used in the present invention is a normal cell or a cell derived from a cancer tissue, and may endogenously express CD1d.

A cell derived from a human, such as a cell isolated and/or purified from an arbitrary human tissue, a cell derived from a particular cell species, an established cell line derived from a human tissue, or a cell differentiated from a stem cell can be used as the normal cell. The normal cell may have an ability to proliferate. A cell isolated and/or purified from a cancer tissue of a patient, or an established cell line derived from a human cancer tissue can be used as the cell derived from a cancer tissue. In this context, the term "isolation" means separation from a living tissue. The term "purification" means separation of a cell derived from a human from one or more of other components contained in a tissue from which the cell is derived. The isolation and purification of cells can be performed by methods known in the art. In one embodiment, the human-derived cell used in the present invention is a normal cell.

The cell isolated and/or purified from an arbitrary human tissue can be a cell derived from an arbitrary human tissue of stomach, small intestine, large intestine, lung, pancreas, kidney, liver, thymus gland, spleen, prostate, ovary, uterus, bone marrow, skin, muscle, peripheral blood, or the like. The cell isolated and/or purified from an arbitrary human tissue may have an ability to proliferate. In one embodiment, the human-derived cell used in the present invention is a non-hemocyte cell.

The cell derived from a particular cell species is a cell derived from a particular cell species of a human tissue (e.g., epithelial cells, endothelial cells, epidermal cells, stromal cells, fibroblasts, adipose tissues, mammary gland cells, mesangial cells, pancreatic β cells, nerve cells, glial cells, exocrine epithelial cells, endocrine cells, skeletal muscle cells, smooth muscle cells, myocardial cells, osteoblasts, embryonic cells, or immune cells (e.g., dendritic cells, macrophages, and B cells)).

Such an established cell line derived from a human tissue can be prepared by use of a method known to those skilled in the art, or is commercially available. Examples of cell lines include human embryonic kidney cell 293 (HEK293) cells (J. Gen. Virol.; 1977; 36: 59-74), WI-38 cells, SC-01MFP cells, and MRC-5 cells, and cells derived from these cells. In one embodiment, the human-derived cell used in the present invention is a cell derived from a HEK293 cell. In one embodiment, the cell derived from a HEK293 cell is a FreeStyle™ 293-F cell.

The cell differentiated from a stem cell is a cell differentiated from a human-derived induced pluripotent stem cell (iPS cell) or embryonic stem cell (ES cell). iPS cells or ES cells and cells derived from these cells can be prepared by use of methods known to those skilled in the art.

The cell derived from a cancer tissue can be obtained by isolation and/or purification from a cancer tissue of a patient by a method known to those skilled in the art. Alternatively, a human cancer tissue-derived established cell line generally available from an institute such as American Type Culture Collection (ATCC®) by those skilled in the art may be used.

2. NY-ESO-1

The aAVC-NY-ESO-1 cell of the present invention comprises a polynucleotide encoding New York esophageal squamous cell carcinoma 1 (NY-ESO-1) or a fragment thereof as a cancer antigen. NY-ESO-1, a protein also called cancer/testis antigen 1 (CTAG1), is found to be expressed in various cancers, but is known to be expressed only in a testis tissue among adult normal tissues.

The NY-ESO-1 used in the present invention may be naturally occurring NY-ESO-1, or may be a modified form thereof as long as the modified form induces NY-ESO-1-specific T cells when administered as aAVC. In one embodiment, the NY-ESO-1 used in the present invention is NY-ESO-1 derived from a mammal (e.g., humans, monkeys, mice, rats, dogs, and chimpanzees). In one embodiment, the NY-ESO-1 is human NY-ESO-1. In one embodiment, the human NY-ESO-1 is a polypeptide consisting of the amino acid sequence set forth in SEQ ID NO: 2. In one embodiment, the human NY-ESO-1 is a polypeptide consisting of an amino acid sequence having at least 90% or more, 95% or more, 96% or more, 97% or more, 98% or more, or 99% or more identity to a polypeptide consisting of the amino acid sequence set forth in SEQ ID NO: 2. In one embodiment, the human NY-ESO-1 is a polypeptide consisting of an amino acid sequence derived from the amino acid sequence set forth in SEQ ID NO: 2 by the deletion, substitution, insertion, and/or addition of 1 or several, preferably 1 to 10, more preferably 1 to 7, still more preferably 1 to 5, 1 to 3, or 1 or 2 amino acids. The NY-ESO-1 used in the present invention may be a fragment of NY-ESO-1 as long as the fragment induces NY-ESO-1-specific T cells when administered as aAVC. In one embodiment, the fragment of NY-ESO-1 is a fragment of human NY-ESO-1. In one embodiment, the fragment of human NY-ESO-1 is a polypeptide having 20% or more, 30% or more, 40% or more, 50% or more, 55% or more, 60% or more, 65% or more, 70% or more, 75% or more, 80% or more, 85% or more, 90% or more, or 95% or more of the length of the amino acid sequence set forth in SEQ ID NO: 2. The induction of NY-ESO-1-specific T cells by administration as aAVC can be evaluated by a method described in, for example, Example 1-2 mentioned later. The polynucleotide encoding NY-ESO-1 or a fragment thereof, used in the present invention can be prepared by designing a nucleotide sequence from the amino acid sequence of the NY-ESO-1 or the fragment thereof used by use of a method known in the art. In one embodiment, the polynucleotide encoding NY-ESO-1 is a polynucleotide consisting of the nucleotide sequence set forth in SEQ ID NO: 1.

In the present specification, the term "identity" means a value of Identity obtained from parameters provided as defaults using EMBOSS Needle (Nucleic Acids Res.; 2015; 43: W580-W584). The parameters described above are as follows:

Gap Open Penalty=10
Gap Extend Penalty=0.5
Matrix=EBLOSUM62
End Gap Penalty=false 3. CD1d The aAVC-NY-ESO-1 cell of the present invention comprises a polynucleotide encoding CD1d. CD1d is an MHC class I-like glycoprotein expressed on cell surface. The CD1d used in the present invention may be naturally occurring CD1d or a modified form thereof as long as the CD1d has a function of CD1d when expressed by the human-derived cell. Examples of the function of CD1d include the ability to bind to a CD1d ligand (e.g., α-GalCer). The ability of CD1d to bind to a CD1d ligand may be easily evaluated by those skilled in the art using a method known in the art. Alternatively, the function of CD1d may be evaluated by using the ability of aAVC to activate human NKT cells as an index. This ability to activate human NKT cells can be evaluated in an in vitro evaluation system described in, for example, FIG. 1 of Non Patent Literature 5. Briefly, the activation of NKT cells can be evaluated by coculturing CD1d-expressing cells cultured in the presence of α-GalCer with NKT cells, and measuring the amount of IFN-γ in the culture solution.

In one embodiment, the CD1d used in the present invention is CD1d derived from a mammal (e.g., humans, monkeys, mice, rats, dogs, and chimpanzees). In one embodiment, the CD1d is human CD1d. In one embodiment, the human CD1d is a polypeptide consisting of the amino acid sequence set forth in SEQ ID NO: 4. In one embodiment, the human CD1d is a polypeptide that consists of an amino acid sequence derived from the amino acid sequence set forth in SEQ ID NO: 4 with the deletion, substitution, insertion, and/or addition of 1 to 10, 1 to 7, 1 to 5, 1 to 3, or 1 or 2 amino acids, and has a function of CD1d. In one embodiment, the human CD1d is a polypeptide that consists of an amino acid sequence having at least 90% or more, 95% or more, 96% or more, 97% or more, 98% or more, or 99% or more identity to a polypeptide shown in SEQ ID NO: 4, and has a function of CD1d.

The polynucleotide encoding CD1d, used in the present invention may be an endogenous polynucleotide of the human-derived cell used, or an exogenously introduced polynucleotide. In the case of exogenously introducing the polynucleotide encoding CD1d to the human-derived cell, the polynucleotide can be prepared by designing a nucleotide sequence from the amino acid sequence of the CD1d used by use of a method known in the art. In one embodiment, the polynucleotide encoding CD1d is a polynucleotide consisting of the nucleotide sequence set forth in SEQ ID NO: 3.

4. Promoter

In the aAVC-NY-ESO-1 cell of the present invention, the polynucleotide encoding NY-ESO-1 or a fragment thereof is operably linked to an inducible promoter. In the present specification, the phrase "operably linked" means a state in which a promoter is linked to a polynucleotide in order to control the expression of the polypeptide in host cells by the promoter. In the aAVC-NY-ESO-1 cell of the present invention, in the case of exogenously introducing the polynucleotide encoding CD1d to the human-derived cell, the polynucleotide may be operably linked to a promoter. In this case, any of a promoter constitutively promoting expression and an inducible promoter can be used as the promoter for the expression of CD1d.

The term "inducible promoter" is a promoter inducibly promoting expression, and refers to a promoter that can induce the expression of a polynucleotide operably linked to the promoter in the presence of an inducer that drives the promoter (in the present specification, also referred to as an "inducer of the inducible promoter" or simply an "inducer"). Examples of the inducible promoter include heat inducible promoters (e.g., heat shock promoter) and drug inducible promoters. In one embodiment, the inducible promoter is a drug inducible promoter. In the present specification, the term "drug inducible promoter" means a promoter that regulates the expression of a polynucleotide operably linked to the promoter through an inducer drug. Examples of the drug inducible promoter include cumate operator sequence, λ operator sequence (e.g., 12×λOp), and an inducible promoter of a tetracycline gene expression induction system (hereinafter, referred to as a "tetracycline inducible promoter"). The cumate operator sequence is inactive in the presence of CymR repressor, but is dissociated from the CymR repressor in the presence of an inducer cumate to induce the expression of a polynucleotide operably linked to the promoter. The 2 operator sequence induces the expression of a polynucleotide operably linked to the promoter in the presence of an inducer, such as coumermycin, which dimerizes an activator (λRep-GyrB-AD) having the ability to activate transcription through dimerization. The tetracycline inducible promoter induces the expression of a polynucleotide operably linked to the promoter in the presence of an inducer tetracycline or a derivative thereof (e.g., doxycycline) and a reverse tetracycline-controlled transactivator (rtTA) (e.g., Tet-On 3G). Examples of the tetracycline inducible promoter include TRE3G promoter. In one embodiment, the drug inducible promoter is a tetracycline inducible promoter. In one embodiment, the tetracycline inducible promoter is TRE3G promoter.

Examples of the promoter constitutively promoting expression include promoters derived from viruses such as CMV (cytomegalovirus), RSV (respiratory syncytial virus), and SV40 (simian virus 40), actin promoter, and EF (elongation factor) 1α promoter.

In the aAVC-NY-ESO-1 cell of the present invention, the expression of NY-ESO-1 or a fragment thereof can be induced by culturing the cell in the presence of the inducer of the inducible promoter. In one embodiment, the aAVC-NY-ESO-1 cell of the present invention expresses NY-ESO-1 or a fragment thereof. In one embodiment, the aAVC-NY-ESO-1 cell of the present invention expresses CD1d and NY-ESO-1 or a fragment thereof. In one embodiment, the lower limit of the expression level of the NY-ESO-1 or the fragment thereof in the aAVC-NY-ESO-1 cell of the present invention may be more than 88 ng, 90 ng or more, 100 ng or more, 150 ng or more, 200 ng or more, 245 ng or more, 250 ng or more, 300 ng or more, 400 ng or more, 500 ng or more, 600 ng or more, 700 ng or more, 800 ng or more, 900 ng or more, 1000 ng or more, 1500 ng or more, 2000 ng or more, 2500 ng or more, 3000 ng or more, 4000 ng or more, 5000 ng or more, 6000 ng or more, 7000 ng or more, 8000 ng or more, 9000 ng or more, or 10000 ng or more, and the upper limit thereof may be 30000 ng or less, 35000 ng or less, 40000 ng or less, 43890 ng or less, 45000 ng or less, 50000 ng or less, 55000 ng or less, or 60000 ng or less, per $10^6$ cells. In one embodiment, the expression level of the NY-ESO-1 or the fragment thereof in the aAVC-NY-ESO-1 cell of the present invention is 89 ng to 50000 ng. In one embodiment, the expression level of the NY-ESO-1 or the fragment thereof in the aAVC-NY-ESO-1 cell of the present invention is 89 ng to 45000 ng. In one embodiment, the expression level of the NY-ESO-1 or the fragment thereof in the aAVC-NY-ESO-1 cell of the present invention is 89 ng to 43890 ng. In one embodiment, the expression level of the NY-ESO-1 or the fragment thereof in the aAVC-NY-ESO-1 cell of the present invention is 89 ng to 40000 ng. In one embodiment, the expression level of the NY-ESO-1 or the fragment thereof in the aAVC-NY-ESO-1 cell of the present invention is 89 ng to 35000 ng. In one embodiment, the expression level of the NY-ESO-1 or the fragment thereof in the aAVC-NY-ESO-1 cell of the present invention is 106 ng to 45000 ng. In one embodiment, the expression level of the NY-ESO-1 or the fragment thereof in the aAVC-NY-ESO-1 cell of the present invention is 106 ng to 43890 ng. In one embodiment, the expression level of the NY-ESO-1 or the fragment thereof in the aAVC-NY-ESO-1 cell of the present invention is 106 ng to 40000 ng. In one embodiment, the expression level of the NY-ESO-1 or the fragment thereof in the aAVC-NY-ESO-1 cell of the present invention is 106 ng to 35000 ng. In one embodiment, the expression level of the NY-ESO-1 or the fragment thereof in the aAVC-NY-ESO-1 cell of the present invention is 245 ng to 45000 ng. In one embodiment, the expression level of the NY-ESO-1 or the fragment thereof in the aAVC-NY-ESO-1 cell of the present invention is 245 ng to 43890 ng. In one embodiment, the expression level of the NY-ESO-1 or the fragment thereof in the aAVC-NY-ESO-1 cell of the present invention is 245 ng to 40000 ng. In one embodiment, the expression level of the NY-ESO-1 or the fragment thereof in the aAVC-NY-ESO-1 cell of the present invention is 245 ng to 35000 ng. In one embodiment, the expression level of the NY-ESO-1 or the fragment thereof in the aAVC-NY-ESO-1 cell of the present invention is 1000 ng to 45000 ng. In one embodiment, the expression level of the NY-ESO-1 or the fragment thereof in the aAVC-NY-ESO-1 cell of the present invention is 1000 ng to 43890 ng. In one embodiment, the expression level of the NY-ESO-1 or the fragment thereof in the aAVC-NY-ESO-1 cell of the present invention is 1000 ng to 40000 ng. In one embodiment, the expression level of the NY-ESO-1 or the fragment thereof in the aAVC-NY-ESO-1 cell of the present invention is 1000 ng to 35000 ng.

5. CD1d Ligand

In one embodiment, in the aAVC-NY-ESO-1 cell of the present invention, a CD1d ligand may be loaded on the cell surface. In the present specification, the phrase "CD1d ligand has been loaded on the cell surface" refers to a state in which the CD1d ligand is bound to the surface of the aAVC cell. The loading of the CD1d ligand onto cell surface may be performed by pulsing cells expressing CD1d with the CD1d ligand (e.g., α-GalCer), as described in the section <Method for preparing aAVC-NY-ESO-1 cell of present invention>. In the present specification, the phrase "pulsing with the CD1d ligand" refers to contact of cells with the CD1d ligand in a culture medium. In aAVC pulsed with the CD1d ligand, the CD1d ligand is loaded on all or at least a part of the CD1d molecules.

Examples of the CD1d ligand used in the present invention include α-galactosylceramide (α-GalCer), α-C-galactosylceramide (α-C-GalCer), 7DW8-5, and isoglobotrihexosylceramide (iGb3). In one embodiment, the CD1d ligand is α-GalCer. α-GalCer, which has a chemical name of (2S,3S,4R)-1-O-(α-D-galactosyl)-N-hexacosanoyl-2-amino-1,3,4-octadecanetriol, is a substance registered under CAS RN: 158021-47-7 and set forth in a molecular formula: $C_{50}H_{99}NO_9$ (molecular weight: 858.34). The α-GalCer may be synthesized according to a technique known in the art, or a commercially available product (e.g., α-Galactosylceramide (Funakoshi Co., Ltd., Cat. KRN7000)) may be used.

<Method for Preparing aAVC-NY-ESO-1 Cell of Present Invention>

The aAVC-NY-ESO-1 cell of the present invention can be prepared by introducing a polynucleotide encoding NY-ESO-1 or a fragment thereof, and, if necessary, a polynucleotide encoding CD1d, to a human-derived cell, wherein the polynucleotide encoding NY-ESO-1 or a fragment thereof is operably linked to an inducible promoter. The method for preparing the aAVC-NY-ESO-1 cell of the present invention may further comprise the steps of: culturing the aAVC-NY-ESO-1 cell; cloning the cell; and loading a CD1d ligand onto the cell surface.

1. Introduction of Polynucleotide to Human-Derived Cell

The aAVC-NY-ESO-1 cell of the present invention can be prepared by introducing a polynucleotide encoding CD1d and a polynucleotide encoding NY-ESO-1 or a fragment thereof to a human-derived cell, wherein the polynucleotide encoding NY-ESO-1 or a fragment thereof is operably linked to an inducible promoter (hereinafter, the polynucleotides to be introduced are also referred to as "polynucleotides of interest"). Alternatively, in the case of using a cell endogenously expressing CD1d as the human-derived cell, the aAVC-NY-ESO-1 cell of the present invention can be prepared by introducing a polynucleotide encoding NY-ESO-1 or a fragment thereof to a human-derived cell endogenously expressing CD1d, wherein the polynucleotide encoding NY-ESO-1 or a fragment thereof is operably linked to an inducible promoter.

The polynucleotide encoding CD1d and the polynucleotide encoding NY-ESO-1 or a fragment thereof can be designed and prepared by use of a standard molecular biological and/or chemical method, for example, by obtaining nucleotide sequences encoding amino acid sequences from NCBI RefSeq ID or GenBank Accession numbers. For example, these polynucleotides can be synthesized by use of a phosphoramidite method based on their nucleotide sequences or can be prepared by combining DNA fragments obtained through polymerase chain reaction (PCR) from cDNA libraries.

The introduction of the polynucleotides of interest to the human-derived cell can be performed by use of any method of a non-viral vector system or a viral vector system, such as electroporation, lipofection, or microinjection. In the case of using a method of a non-viral vector system, the polynucleotides of interest may be in a form such as a plasmid vector or cDNA or in a mRNA form.

The plasmid vector or the viral vector can be used as an expression vector for the exogenous expression of CD1d or NY-ESO-1 or a fragment thereof in the human-derived cell. The expression vector is not particularly limited as long as the expression vector permits expression of the polypeptide of interest. The expression vector can be prepared by use of a method known to those skilled in the art. For the expression vector, for example, pcDNA series (Thermo Fisher Scientific Inc.), pALTER®-MAX (Promega Corp.), or pHEK293 Ultra Expression Vector (Takara Bio Inc.) can be used as the plasmid vector, and, for example, lentivirus, adenovirus, retrovirus, or adeno-associated virus can be used as the viral vector. For example, in the case of using lentivirus in the introduction of the polynucleotides of interest to the human-derived cell, the lentivirus can be prepared using pLVSIN-CMV/EF1α vector (Takara Bio Inc.) or pLenti vector (Thermo Fisher Scientific Inc.). When the human-derived cell is caused to exogenously express CD1d and NY-ESO-1 or a fragment thereof, the polynucleotide encoding CD1d and the polynucleotide encoding NY-ESO-1 or a fragment thereof may be introduced to the human-derived cell using one expression vector, or may be introduced thereto using separate expression vectors. The expression vector may also contain a gene capable of serving as a marker (e.g., a drug resistance gene, a gene encoding a reporter enzyme, or a gene encoding a fluorescent protein) for confirming the expression of the gene or the polynucleotide of interest. The expression vector may further contain a start codon and a stop codon, an enhancer sequence, an untranslated region, a splice junction, a polyadenylation site, or a replicable unit, etc.

In one embodiment, the method for preparing the aAVC-NY-ESO-1 cell of the present invention comprises the step of introducing an expression vector comprising a polynucleotide encoding CD1d and an expression vector comprising a polynucleotide encoding NY-ESO-1 or a fragment thereof to a human-derived cell, wherein the polynucleotide encoding NY-ESO-1 or a fragment thereof is operably linked to an inducible promoter. In one embodiment, the method for preparing the aAVC-NY-ESO-1 cell of the present invention comprises the step of introducing an expression vector comprising a polynucleotide encoding CD1d and a polynucleotide encoding NY-ESO-1 or a fragment thereof to a human-derived cell, wherein the polynucleotide encoding NY-ESO-1 or a fragment thereof is operably linked to an inducible promoter. In one embodiment, the method for preparing the aAVC-NY-ESO-1 cell of the present invention comprises the step of introducing an expression vector comprising a polynucleotide encoding NY-ESO-1 or a fragment thereof to a human-derived cell endogenously expressing CD1d, wherein the polynucleotide encoding NY-ESO-1 or a fragment thereof is operably linked to an inducible promoter. In one embodiment as to these methods, the expression vector is a plasmid vector or a viral vector. In one embodiment, the expression vector is a viral vector. In one embodiment, the viral vector is a lentivirus vector.

In one embodiment, the aAVC-NY-ESO-1 cell of the present invention is a cell prepared by introducing an expression vector comprising a polynucleotide encoding CD1d and an expression vector comprising a polynucleotide encoding NY-ESO-1 or a fragment thereof to a human-derived cell, wherein the polynucleotide encoding NY-ESO-1 or a fragment thereof is operably linked to an inducible promoter. In one embodiment, the aAVC-NY-ESO-1 cell of the present invention is a cell prepared by introducing an expression vector comprising a polynucleotide encoding CD1d and a polynucleotide encoding NY-ESO-1 or a fragment thereof to a human-derived cell, wherein the polynucleotide encoding NY-ESO-1 or a fragment thereof is operably linked to an inducible promoter. In one embodiment, the aAVC-NY-ESO-1 cell of the present invention is a cell prepared by introducing an expression vector comprising a polynucleotide encoding NY-ESO-1 or a fragment thereof to a human-derived cell endogenously expressing CD1d, wherein the polynucleotide encoding NY-ESO-1 or a fragment thereof is operably linked to an inducible promoter. In one embodiment as to these cells, the expression vector is a plasmid vector or a viral vector. In one embodiment, the expression vector is a viral vector. In one embodiment, the viral vector is a lentivirus vector. In one embodiment, the prepared aAVC-NY-ESO-1 cell has the polynucleotide encoding CD1d and the polynucleotide encoding NY-ESO-1 or a fragment thereof extrachromosomally or on genomic DNA of the cell nucleus, wherein the polynucleotide encoding NY-ESO-1 or a fragment thereof is operably linked to an inducible promoter. In one embodiment, the prepared cell has the polynucleotide encoding CD1d and the polynucleotide encoding NY-ESO-1 or a fragment thereof on genomic DNA of the cell nucleus, wherein the polynucleotide encoding NY-ESO-1 or a fragment thereof is operably linked to an inducible promoter.

2. Culture of aAVC-NY-ESO-1 Cell

The aAVC-NY-ESO-1 cell prepared by the method described above can be further caused to proliferate by culture. The cell culture for the maintenance or proliferation of the aAVC-NY-ESO-1 cell is performed by a method known in the art. For example, MEM medium (Science; 1952; 122: 501), DMEM medium (Virology; 1959; 8: 396-397), RPMI1640 medium (J. Am. Med. Assoc.; 1967; 199: 519-524), 199 medium (Proc. Soc. Exp. Biol. Med.; 1950;

73: 1-8), FreeStyle™ 293 Expression Medium (Thermo Fisher Scientific Inc., Cat. 12338022), CD 293 Medium (Thermo Fisher Scientific Inc., Cat. 11913019), or Expi293™ Expression Medium (Thermo Fisher Scientific Inc., Cat. A1435101) can be used as a basal medium. The culture medium can contain, for example, serum (e.g., fetal bovine serum), a serum replacement (e.g., KnockOut Serum Replacement: KSR), a fatty acid or a lipid, an amino acid, vitamin, a growth factor, a cytokine, an antioxidant, 2-mercaptoethanol, pyruvic acid, a buffer, an inorganic salt, or an antibiotic. In one embodiment, the medium for use in culture is a serum-free medium or a chemically defined medium.

The culture conditions (e.g., culture conditions such as culture time, temperature, medium pH, and $CO_2$ concentration) can be appropriately selected by those skilled in the art. The medium pH is preferably approximately 6 to 8. The culture temperature is not particularly limited and is, for example, approximately 30 to 40° C., preferably approximately 37° C. The $CO_2$ concentration is approximately 1 to 10%, preferably approximately 5%. The culture time is not particularly limited, and the culture is performed for approximately 15 to 336 hours. If necessary, aeration or stirring may be performed.

At the time of culture of the aAVC-NY-ESO-1 cell, the expression of NY-ESO-1 or a fragment thereof may be induced by contacting the aAVC-NY-ESO-1 cells with an inducer of the inducible promoter. In one embodiment, the method for preparing the aAVC-NY-ESO-1 cell comprises the step of culturing the aAVC-NY-ESO-1 cell in the presence of an inducer of the inducible promoter, thereby inducing the expression of NY-ESO-1 or a fragment thereof. In one embodiment, the inducible promoter is a drug inducible promoter, and the preparation method comprises the step of culturing the aAVC-NY-ESO-1 cell in the presence of an inducer of the drug inducible promoter. In the case of using a drug inducible promoter, the expression of a gene or a polynucleotide operably linked to the drug inducible promoter may be induced by culturing the cell in a medium supplemented with an inducer drug such as tetracycline, doxycycline, cumate, or coumermycin. This step can be performed in accordance with a gene induction method using a general gene induction system. In one embodiment, the drug inducible promoter is a tetracycline inducible promoter, and the preparation method comprises the step of culturing the aAVC-NY-ESO-1 cell in the presence of a tetracycline or a derivative thereof and rtTA. In one embodiment, the tetracycline inducible promoter is TRE3G promoter, and the preparation method comprises the step of culturing the aAVC-NY-ESO-1 cell in the presence of tetracycline or a derivative thereof and Tet-On 3G. The expression levels of the CD1d and the NY-ESO-1 or the fragment thereof in the obtained aAVC-NY-ESO-1 cell can be measured by a method known to those skilled in the art, such as Western blot, ELISA, or flow cytometry using an anti-CD1d antibody or an anti-NY-ESO-1 antibody.

3. Cloning of aAVC-NY-ESO-1 Cell

In the case of introducing a polynucleotide to cells, there coexist cells to which the polynucleotide of interest has been introduced and cells to which the polynucleotide of interest has not been introduced. Further, in the case of integrating a polynucleotide of interest onto genomic DNA of a cell nucleus, the integration location also differs depending on cells. Thus, those cells may be a heterogeneous population. In the present specification, the heterogeneous population of cells is referred to as a "cell pool". Single cells to which the polynucleotide encoding CD1d and the polynucleotide encoding NY-ESO-1 or a fragment thereof have been introduced, wherein the polynucleotide encoding NY-ESO-1 or a fragment thereof is operably linked to an inducible promoter (hereinafter, referred to as "cloned cells") can be obtained by a method for obtaining cells having a single genotype from the cell pool (in the present specification, referred to as "cloning") and caused to proliferate, thereby obtaining a cell population having a single genotype (hereinafter, referred to as a "population of cloned cells"). The cloning of the aAVC-NY-ESO-1 cell can be carried out by use of a method well known to those skilled in the art. For example, a limiting dilution method, a single-cell sorting method, or a colony pickup method can be used. In one embodiment, the method for cloning the aAVC-NY-ESO-1 cell may employ one method or a combination of two or more methods selected from a limiting dilution method, a single-cell sorting method, and a colony pickup method. In one embodiment, the method for cloning the aAVC-NY-ESO-1 cell is a limiting dilution method.

For each clone of aAVC-NY-ESO-1 cells obtained by the above method, by contacting a part of the cells of the clone with an inducer of an inducible promoter and measuring the expression level of CD1d and NY-ESO-1 or a fragment thereof in each clone, a population of cloned aAVC-NY-ESO-1 cells that show the desired expression levels for CD1d and NY-ESO-1 or fragments thereof in the presence of the inducer can be selected. The selected population of cloned cells may be preserved in a frozen state (also referred to as "frozen product") and used as a research cell bank (RCB). The cells of RCB may be cultured for proliferation, then frozen, and used as a master cell bank (MCB). The cells of MCB may be cultured for proliferation, then frozen, and used as a working cell bank (WCB). The cells of WCB may be cultured and used as a pharmaceutical raw material. Each cell bank may contain a cryopreserving agent. Each cell bank may be dispensed to a plurality of containers (e.g., 2 to 10000 containers, for example, 10 to 1000 containers, for example, 100 to 500 containers) and stored in a frozen state. The thawing, culture, and contact with the inducer, of the cloned aAVC-NY-ESO-1 cells, and the measurement of the expression levels of the CD1d and the NY-ESO-1 or the fragment thereof can each be performed by a method known to those skilled in the art. The culture, the contact with the inducer, and the measurement of the expression levels can be performed by use of, for example, a method described in "2. Culture of aAVC-NY-ESO-1 cell". In one embodiment, the culture and contact with the inducer, of the cloned aAVC-NY-ESO-1 cells, and the measurement of the expression levels of the CD1d and the NY-ESO-1 or the fragment thereof can be performed after thawing of RCB and WCB.

In one embodiment, the lower limit of the expression level of the NY-ESO-1 or the fragment thereof in the resulting aAVC-NY-ESO-1 cell is more than 88 ng, 90 ng or more, 100 ng or more, 150 ng or more, 200 ng or more, 245 ng or more, 250 ng or more, 300 ng or more, 400 ng or more, 500 ng or more, 600 ng or more, 700 ng or more, 800 ng or more, 900 ng or more, 1000 ng or more, 1500 ng or more, 2000 ng or more, 2500 ng or more, 3000 ng or more, 4000 ng or more, 5000 ng or more, 6000 ng or more, 7000 ng or more, 8000 ng or more, 9000 ng or more, or 10000 ng or more, and the upper limit thereof is 30000 ng or less, 35000 ng or less, 40000 ng or less, 43890 ng or less, 45000 ng or less, 50000 ng or less, 55000 ng or less, or 60000 ng or less as the upper limit value, per $10^6$ cells. In one embodiment, the expression level of the NY-ESO-1 or the fragment thereof in the resulting aAVC-NY-ESO-1 cell is 89 ng to 50000 ng. In one embodiment, the expression level of the NY-ESO-1 or the fragment thereof in the resulting aAVC-NY-ESO-1 cell is 89 ng to 45000 ng. In one embodiment, the expression level of the NY-ESO-1 or the fragment thereof in the resulting aAVC-NY-ESO-1 cell is 89 ng to 43890 ng. In one embodiment, the expression level of the NY-ESO-1 or the fragment thereof in the resulting aAVC-NY-ESO-1 cell is 89 ng to 40000 ng. In one embodiment, the expression level of the NY-ESO-1 or the fragment thereof in the resulting aAVC-NY-ESO-1 cell is 89 ng to 35000 ng. In one embodiment, the expression level of the NY-ESO-1 or the fragment thereof in the resulting aAVC-NY-ESO-1 cell is 106 ng to 45000 ng. In one embodiment, the expression level of the NY-ESO-1 or the fragment thereof in the resulting aAVC-NY-ESO-1 cell is 106 ng to 43890 ng. In one embodiment, the expression level of the NY-ESO-1 or the fragment thereof in the resulting aAVC-NY-ESO-1 cell is 106 ng to 40000 ng. In one embodiment, the expression level of the NY-ESO-1 or the fragment thereof in the resulting aAVC-NY-ESO-1 cell is 106 ng to 35000 ng. In one embodiment, the expression level of the NY-ESO-1 or the fragment thereof in the resulting aAVC-NY-ESO-1 cell is 245 ng to 45000 ng. In one embodiment, the expression level of the NY-ESO-1 or the fragment thereof in the resulting aAVC-NY-ESO-1 cell is 245 ng to 43890 ng. In one embodiment, the expression level of the NY-ESO-1 or the fragment thereof in the resulting aAVC-NY-ESO-1 cell is 245 ng to 40000 ng. In one embodiment, the expression level of the NY-ESO-1 or the fragment thereof in the resulting aAVC-NY-ESO-1 cell is 245 ng to 35000 ng. In one embodiment, the expression level of the NY-ESO-1 or the fragment thereof in the resulting aAVC-NY-ESO-1 cell is 1000 ng to 45000 ng. In one embodiment, the expression level of the NY-ESO-1 or the fragment thereof in the resulting aAVC-NY-ESO-1 cell is 1000 ng to 43890 ng. In one embodiment, the expression level of the NY-ESO-1 or the fragment thereof in the resulting aAVC-NY-ESO-1 cell is 1000 ng to 40000 ng. In one embodiment, the expression level of the NY-ESO-1 or the fragment thereof in the resulting aAVC-NY-ESO-1 cell is 1000 ng to 35000 ng.

4. Loading of CD1d Ligand onto aAVC-NY-ESO-1 Cell

An aAVC-NY-ESO-1 cell with a CD1d ligand loaded thereon can be prepared by pulsing the aAVC-NY-ESO-1 cell with the CD1d ligand. The conditions for pulsing with the CD1d ligand (e.g., the timing of adding the CD1d ligand to a cell culture medium, the concentration of the CD1d ligand in the culture medium and culture time) can be appropriately adjusted by those skilled in the art in consideration of the cell used and culture conditions. The concentration of the CD1d ligand to be added to the culture medium for the aAVC-NY-ESO-1 cell is not particularly limited and can be appropriately selected within the range of, for example, 1 ng/mL to 10000 ng/mL. In one embodiment, the CD1d ligand is α-GalCer. In one embodiment, the loading of the CD1d ligand onto the aAVC-NY-ESO-1 cell may be performed before contact of the cell with the inducer. In one embodiment, the loading of the CD1d ligand onto the aAVC-NY-ESO-1 cell may be performed after contact of the cell with the inducer. In one embodiment, the loading of the CD1d ligand onto the aAVC-NY-ESO-1 cell may be performed at the same time with contact of the cell with the inducer. In these embodiments, the aAVC-NY-ESO-1 cell is preferably a cloned cell.

In the thus-prepared aAVC-NY-ESO-1 cell expressing CD1d and NY-ESO-1 or a fragment thereof and with CD1d ligand loaded thereon, the cell proliferation may be arrested by an artificial method. The method for arresting the proliferation of the cell is not particularly limited. For example, a method of arresting cell proliferation by exposure to radiation of a radioactive ray (e.g., X-ray), or a method of adding a drug such as mitomycin C may be used. In one embodiment, the aAVC-NY-ESO-1 cell of the present invention may be a cell expressing CD1d and NY-ESO-1 or a fragment thereof with its proliferation arrested. In one embodiment, the aAVC-NY-ESO-1 cell of the present invention may be a cell expressing CD1d and NY-ESO-1 or a fragment thereof with a CD1d ligand loaded thereon and its proliferation arrested.

<Pharmaceutical Composition, Etc. of Present Invention>

The present invention also provides a pharmaceutical composition comprising the aAVC-NY-ESO-1 cell of the present invention. In the pharmaceutical composition, the aAVC-NY-ESO-1 cell expresses CD1d and NY-ESO-1 or a fragment thereof, and has a CD1d ligand loaded on the surface of the cell. In one embodiment, the pharmaceutical composition is a pharmaceutical composition for use in treating a cancer. In one embodiment, the CD1d ligand is α-GalCer. The pharmaceutical composition can be prepared by a commonly used method using an excipient commonly used in the art, i.e., an excipient for a drug, a carrier for a drug, or the like. For the formulation of the pharmaceutical composition, an excipient, a carrier, an additive, or the like appropriate for its dosage form can be used within a pharmaceutically acceptable range. Examples of the dosage form of the pharmaceutical composition include parenteral agents such as injections and agents for drip infusions. In one embodiment, the pharmaceutical composition of the present invention may comprise a frozen product of the aAVC-NY-ESO-1 cell. In one embodiment, the pharmaceutical composition of the present invention may comprise a frozen product of the aAVC-NY-ESO-1 cell and a cryopreserving agent. In one embodiment, the pharmaceutical composition of the present invention may comprise a suspension of the aAVC-NY-ESO-1 cell. In one embodiment, the pharmaceutical composition of the present invention may comprise a suspension of the aAVC-NY-ESO-1 cell and a cryopreserving agent. The present invention also provides use of the aAVC-NY-ESO-1 cell of the present invention for manufacturing a pharmaceutical composition for use in treating a cancer, wherein the cell expresses CD1d and NY-ESO-1 or a fragment thereof, and has a CD1d ligand loaded on the surface of the cell. In one embodiment, the CD1d ligand is α-GalCer. The present invention also provides the aAVC-NY-ESO-1 cell of the present invention for treating a cancer, wherein the cell expresses CD1d and NY-ESO-1 or a fragment thereof, and has a CD1d ligand loaded on the surface of the cell. In one embodiment, the CD1d ligand is α-GalCer.

The present invention also provides a method for treating a cancer, comprising the step of administering the aAVC-NY-ESO-1 cell of the present invention to a subject. In the method, the aAVC-NY-ESO-1 cell expresses CD1d and NY-ESO-1 or a fragment thereof, and has a CD1d ligand loaded on the surface of the cell. In one embodiment, the CD1d ligand is α-GalCer. In the present specification, the term "subject" is a mammal (e.g., humans, monkeys, mice, rats, dogs, and chimpanzees). In one embodiment, the subject is a human. In the present specification, the term "treatment" is used in a meaning including therapeutic treatment and prophylactic treatment. In the case of administering the aAVC-NY-ESO-1 cell to a subject, the aAVC-NY-ESO-1 cell can be administered in the form of a pharmaceutical composition comprising this cell and a pharmaceutically acceptable excipient to the subject. The dose of the aAVC-NY-ESO-1 cell to the subject and the number of doses thereof can be appropriately adjusted according to the type, position, and severity of the cancer, the age, body weight and condition of the subject to be treated, etc. For example, $1\times10^3$ cells/kg to $1\times10^9$ cells/kg per dose to the subject can be used as the dose of the aAVC-NY-ESO-1 cell. As for a method for administering the aAVC-NY-ESO-1 cell to the subject, the cell can be administered by, for example, intravenous, intratumoral, intradermal, subcutaneous, intramuscular, intraperitoneal, or intra-arterial injection or drip infusion. The treatment method of the present invention can be used in combination with an additional cancer therapy method. Examples of the additional cancer therapy method include surgery, radiotherapy, hematopoietic stem cell transplantation, and therapy with other anticancer agents.

Examples of the cancer to be targeted by treating the present invention include, but are not particularly limited to: blood cancers such as acute lymphoblastic leukemia (ALL), acute myeloid leukemia (AML), Hodgkin's lymphoma, non-Hodgkin's lymphoma, B cell lymphoma, multiple myeloma, and T cell lymphoma; solid cancers such as myelodysplastic syndrome, adenocarcinoma, squamous cell carcinoma, adenosquamous carcinoma, anaplastic cancer, large-cell cancer, non-small cell lung cancer, small-cell lung cancer, mesothelioma, skin cancer, breast cancer, prostate cancer, bladder cancer, vaginal cancer, neck cancer, head and neck cancer, uterine cancer, cervical cancer, liver cancer, gallbladder cancer, bile duct cancer, kidney cancer, pancreatic cancer, lung cancer, colon cancer, large intestinal cancer, rectum cancer, small intestinal cancer, stomach cancer, esophageal cancer, testis cancer, ovary cancer, and brain tumor; cancers of bone tissues, cartilage tissues, adipose tissues, muscle tissues, vascular tissues and hematopoietic tissues; sarcomas such as chondrosarcoma, Ewing's sarcoma, malignant hemangioendothelioma, malignant schwannoma, osteosarcoma, and soft tissue sarcoma; and blastomas such as hepatoblastoma, medulloblastoma, nephroblastoma, neuroblastoma, pancreatoblastoma, pleuropulmonary blastoma, and retinoblastoma. In one embodiment, the cancer to be targeted by treating the present invention is a NY-ESO-1-positive cancer.

In the pharmaceutical composition, the use, the cell, and the cancer treatment method of the present invention, the lower limit of the expression level of the NY-ESO-1 or the fragment thereof in the aAVC-NY-ESO-1 cell may be, for example, more than 88 ng, 90 ng or more, 100 ng or more, 150 ng or more, 200 ng or more, 245 ng or more, 250 ng or more, 300 ng or more, 400 ng or more, 500 ng or more, 600 ng or more, 700 ng or more, 800 ng or more, 900 ng or more, 1000 ng or more, 1500 ng or more, 2000 ng or more, 2500 ng or more, 3000 ng or more, 4000 ng or more, 5000 ng or more, 6000 ng or more, 7000 ng or more, 8000 ng or more, 9000 ng or more, or 10000 ng or more, and the upper limit thereof may be 30000 ng or less, 35000 ng or less, 40000 ng or less, 43890 ng or less, 45000 ng or less, 50000 ng or less, 55000 ng or less, or 60000 ng or less as the upper limit value, per $10^6$ cells. In one embodiment, the expression level of the NY-ESO-1 or the fragment thereof in the aAVC-NY-ESO-1 cell is more than 88 ng, 90 ng or more, 100 ng or more, 150 ng or more, 200 ng or more, 245 ng or more, 250 ng or more, 300 ng or more, 400 ng or more, 500 ng or more, 600 ng or more, 700 ng or more, 800 ng or more, 900 ng or more, 1000 ng or more, 1500 ng or more, 2000 ng or more, 2500 ng or more, 3000 ng or more, 4000 ng or more, 5000 ng or more, 6000 ng or more, 7000 ng or more, 8000 ng or more, 9000 ng or more, or 10000 ng or more as the lower limit value, and 30000 ng or less, 35000 ng or less, 40000 ng or less, 43890 ng or less, 45000 ng or less, 50000 ng or less, 55000 ng or less, or 60000 ng or less as the upper limit value, per $10^6$ cells. In one embodiment, the expression level of the NY-ESO-1 or the fragment thereof in the aAVC-NY-ESO-1 cell is 89 ng to 50000 ng. In one embodiment, the expression level of the NY-ESO-1 or the fragment thereof in the aAVC-NY-ESO-1 cell is 89 ng to 45000 ng. In one embodiment, the expression level of the NY-ESO-1 or the fragment thereof in the aAVC-NY-ESO-1 cell is 89 ng to 43890 ng. In one embodiment, the expression level of the NY-ESO-1 or the fragment thereof in the aAVC-NY-ESO-1 cell is 89 ng to 40000 ng. In one embodiment, the expression level of the NY-ESO-1 or the fragment thereof in the aAVC-NY-ESO-1 cell is 89 ng to 35000 ng. In one embodiment, the expression level of the NY-ESO-1 or the fragment thereof in the aAVC-NY-ESO-1 cell is 106 ng to 45000 ng. In one embodiment, the expression level of the NY-ESO-1 or the fragment thereof in the aAVC-NY-ESO-1 cell is 106 ng to 43890 ng. In one embodiment, the expression level of the NY-ESO-1 or the fragment thereof in the aAVC-NY-ESO-1 cell is 106 ng to 40000 ng. In one embodiment, the expression level of the NY-ESO-1 or the fragment thereof in the aAVC-NY-ESO-1 cell is 106 ng to 35000 ng. In one embodiment, the expression level of the NY-ESO-1 or the fragment thereof in the aAVC-NY-ESO-1 cell is 245 ng to 45000 ng. In one embodiment, the expression level of the NY-ESO-1 or the fragment thereof in the aAVC-NY-ESO-1 cell is 245 ng to 43890 ng. In one embodiment, the expression level of the NY-ESO-1 or the fragment thereof in the aAVC-NY-ESO-1 cell is 245 ng to 40000 ng. In one embodiment, the expression level of the NY-ESO-1 or the fragment thereof in the aAVC-NY-ESO-1 cell is 245 ng to 35000 ng. In one embodiment, the expression level of the NY-ESO-1 or the fragment thereof in the aAVC-NY-ESO-1 cell is 1000 ng to 45000 ng. In one embodiment, the expression level of the NY-ESO-1 or the fragment thereof in the aAVC-NY-ESO-1 cell is 1000 ng to 43890 ng. In one embodiment, the expression level of the NY-ESO-1 or the fragment thereof in the aAVC-NY-ESO-1 cell is 1000 ng to 40000 ng. In one embodiment, the expression level of the NY-ESO-1 or the fragment thereof in the aAVC-NY-ESO-1 cell is 1000 ng to 35000 ng.

<Method for Producing Cell or Pharmaceutical Composition for Use in Treatment of Cancer>

The present invention also provides a method for producing a cell or a pharmaceutical composition for use in treating a cancer, comprising the step of contacting the aAVC-NY-ESO-1 cell of the present invention with an inducer of the inducible promoter to induce the expression of NY-ESO-1 or a fragment thereof. In one embodiment, the production method comprises the step of culturing the aAVC-NY-ESO-1 cell in the presence of an inducer of the inducible promoter, thereby inducing the expression of NY-ESO-1 or a fragment thereof. In one embodiment, the production method further comprises the step of loading α-GalCer onto the cell surface. The loading of the CD1d ligand onto the cell surface may be performed before, after, or at the same time with contact of the aAVC-NY-ESO-1 cell with the inducer. The present invention also provides use of the aAVC-NY-ESO-1 cell of the present invention in the manufacture of a pharmaceutical composition for use in treating a cancer.

The present invention also provides a method for producing a cell or a pharmaceutical composition for use in treating a cancer, comprising the step of:

introducing a polynucleotide encoding CD1d and a polynucleotide encoding NY-ESO-1 or a fragment thereof to a human-derived cell, wherein the polynucleotide encoding NY-ESO-1 or a fragment thereof is operably linked to an inducible promoter; or introducing a polynucleotide encoding NY-ESO-1 or a fragment thereof to a human-derived cell endogenously expressing CD1d, wherein the polynucleotide encoding NY-ESO-1 or a fragment thereof is operably linked to an inducible promoter.

In one embodiment, the production method further comprises the step of contacting the cell obtained in the step (aAVC-NY-ESO-1 cell) with an inducer of the inducible promoter to induce the expression of NY-ESO-1 or a fragment thereof. In one embodiment, the production method comprises the step of culturing the aAVC-NY-ESO-1 cell in the presence of an inducer of the inducible promoter, thereby inducing the expression of NY-ESO-1 or a fragment thereof. In one embodiment, the production method further comprises the step of loading α-GalCer onto the cell surface. The loading of the CD1d ligand onto the cell surface may be performed before, after, or at the same time with contact of the aAVC-NY-ESO-1 cell with the inducer.

Specific embodiments regarding the cell and the steps, etc. for use in the production method described in this section are as described in the preceding sections <aAVC-NY-ESO-1 cell of present invention> and <Method for preparing aAVC-NY-ESO-1 cell of present invention>.

<Combined Use of aAVC-NY-ESO-1 Cell of Present Invention and Immune Checkpoint Inhibitor>

The present invention also provides a method for treating a cancer, comprising the step of administering the aAVC-NY-ESO-1 cell of the present invention and an immune checkpoint inhibitor to a subject. The present invention also provides a pharmaceutical composition for treating a cancer, comprising the aAVC-NY-ESO-1 cell of the present invention, wherein the pharmaceutical composition is used in combination with an immune checkpoint inhibitor. The present invention also provides the aAVC-NY-ESO-1 cell of the present invention for treating a cancer, wherein the aAVC-NY-ESO-1 cell of the present invention is used in combination with an immune checkpoint inhibitor. The present invention also provides use of the aAVC-NY-ESO-1 cell of the present invention for producing a pharmaceutical composition for use in treating a cancer, wherein the pharmaceutical composition is used in combination with an immune checkpoint inhibitor. In the method, the pharmaceutical composition, the cell or the use, the aAVC-NY-ESO-1 cell of the present invention expresses CD1d and NY-ESO-1 or a fragment thereof, and a CD1d ligand is loaded on the surface of the cell.

In the present specification, the "immune checkpoint inhibitor" means a medicament that stimulates the immunity by canceling the suppression of immune cells caused by an immune checkpoint molecule. Examples of the immune checkpoint molecule include programmed cell death 1 (PD-1), cytotoxic T-lymphocyte-associated protein 4 (CTLA-4), T-cell immunoglobulin domain and mucin domain-3 (TIM-3), lymphocyte activation gene 3 (LAG-3), and V-type immunoglobulin domain-containing suppressor of T-cell activation (VISTA). The immune checkpoint to be formed by such a molecule is called PD-1 immune checkpoint, CTLA-4 immune checkpoint, TIM-3 immune checkpoint, LAG-3 immune checkpoint, and VISTA immune checkpoint. The immune checkpoint inhibitor is capable of inhibiting the functions of the immune checkpoint, for example, by binding to an immune checkpoint molecule or a ligand thereof. For example, the PD-1 immune checkpoint inhibitor can inhibit the PD-1 immune checkpoint by inhibiting the binding of PD-1 to PD-L1 or PD-L2. The CTLA-4 immune checkpoint inhibitor can inhibit the CTLA-4 immune checkpoint by inhibiting the binding of CTLA-4 to CD80 or CD86. The TIM-3 immune checkpoint inhibitor can inhibit the TIM-3 immune checkpoint by inhibiting the binding of TIM-3 to galectin-9. The LAG-3 immune checkpoint inhibitor can inhibit the LAG-3 immune checkpoint by inhibiting the binding of LAG-3 to an MHC class II molecule. The VISTA immune checkpoint inhibitor can inhibit the VISTA immune checkpoint by inhibiting the binding of VISTA to VSIG-3/IGSF11. The immune checkpoint inhibitor refers to a substance that can inhibit one or more of immune checkpoints such as PD-1 immune checkpoint, CTLA-4 immune checkpoint, TIM-3 immune checkpoint, LAG3 immune checkpoint, and VISTA immune checkpoint. Examples thereof include antibodies, antigen binding proteins, and low molecular compounds. Some antibodies bind to either a receptor or a ligand. Examples of the antibody inhibiting the PD-1 immune checkpoint include anti-PD-1 antibodies, anti-PD-L1 antibodies, and anti-PD-L2 antibodies. For example, nivolumab, pembrolizumab, MK-3475, AMP-224, pidilizumab, AMP-514, ANB-011, BGB-A317, REGN-2810, HR301210, PF-06801591, JS-001, IBI-308, CBT-501, avelumab, atezolizumab, BMS-936559, LY-3300054, JNJ-61610588, and durvalumab may be used. Examples of the antibody inhibiting the CTLA-4 immune checkpoint include anti-CTLA-4 antibodies, anti-CD80 antibodies, and anti-CD86 antibodies. For example, ipilimumab and tremelimumab may be used. Examples of the antibody inhibiting the TIM-3 immune checkpoint include anti-TIM-3 antibodies and anti-galectin-9 antibodies. For example, MGB453 may be used. Examples of the antibody inhibiting the VISTA immune checkpoint include an antibody selected from the group consisting of anti-VISTA antibodies and anti-VSIG-3/IGSF11 antibodies. For example, JNJ-61610588 may be used. Alternatively, AUPM-170 may be used as the low-molecular compound.

Combined use of the aAVC-NY-ESO-1 cell of the present invention and the immune checkpoint inhibitor may enhance the antitumor effect of the aAVC-NY-ESO-1 cell. In one embodiment, the immune checkpoint inhibitor that may be used in combination with the aAVC-NY-ESO-1 cell of the present invention is a PD-1 immune checkpoint inhibitor. In one embodiment, the immune checkpoint inhibitor for combined use with the aAVC-NY-ESO-1 cell of the present invention is an anti-PD-1 antibody, an anti-PD-L1 antibody, or an anti-PD-L2 antibody. In one embodiment, the immune checkpoint inhibitor for combined use with the aAVC-NY-ESO-1 cell of the present invention is nivolumab, pembrolizumab, avelumab, atezolizumab, or durvalumab. In one embodiment, the immune checkpoint inhibitor for combined use with the aAVC-NY-ESO-1 cell of the present invention is nivolumab or pembrolizumab. In one embodiment, the immune checkpoint inhibitor for combined use with the aAVC-NY-ESO-1 cell of the present invention is pembrolizumab. In another embodiment, the immune checkpoint inhibitor that may be used in combination with the aAVC-NY-ESO-1 cell of the present invention is a CTLA-4 immune checkpoint inhibitor. In one embodiment, the immune checkpoint inhibitor for combined use with the aAVC-NY-ESO-1 cell of the present invention is an anti-CTLA-4 antibody, an anti-CD80 antibody, or an anti-CD86 antibody. In one embodiment, the immune checkpoint inhibitor for combined use with the aAVC-NY-ESO-1 cell of the present invention is ipilimumab or tremelimumab. In one embodiment, the immune checkpoint inhibitor for combined use with the aAVC-NY-ESO-1 cell of the present invention is nivolumab or pembrolizumab. In one embodiment, the immune checkpoint inhibitor for combined use with the aAVC-NY-ESO-1 cell of the present invention is ipilimumab.

For example, in the method for treating a cancer, comprising administering the aAVC-NY-ESO-1 cell of the present invention and an immune checkpoint inhibitor to a subject, in one embodiment, the immune checkpoint inhibitor to be administered to a subject is a PD-1 immune checkpoint inhibitor or a CTLA-4 immune checkpoint inhibitor. In one embodiment, the immune checkpoint inhibitor to be administered to a subject is a PD-1 immune checkpoint inhibitor. In one embodiment, the immune checkpoint inhibitor to be administered to a subject is an anti-PD-1 antibody, an anti-PD-L1 antibody, or an anti-PD-L2 antibody. In one embodiment, the immune checkpoint inhibitor to be administered to a subject is nivolumab, pembrolizumab, avelumab, atezolizumab, or durvalumab. In one embodiment, the immune checkpoint inhibitor to be administered to a subject is nivolumab or pembrolizumab. In one embodiment, the immune checkpoint inhibitor that is used in combination with the aAVC-NY-ESO-1 cell of the present invention is pembrolizumab. In another embodiment, the immune checkpoint inhibitor that can be used in combination with the aAVC-NY-ESO-1 cell of the present invention is a CTLA-4 immune checkpoint inhibitor. In one embodiment, the immune checkpoint inhibitor to be administered to a subject is an anti-CTLA-4 antibody, an anti-CD80 antibody, or an anti-CD86 antibody. In one embodiment, the immune checkpoint inhibitor to be administered to a subject is ipilimumab or tremelimumab. In one embodiment, the immune checkpoint inhibitor to be administered to a subject is nivolumab or pembrolizumab. In one embodiment, the immune checkpoint inhibitor to be administered to a subject is ipilimumab.

The aAVC-NY-ESO-1 cell of the present invention and the immune checkpoint inhibitor may be administered concurrently, successively, continuously, or in an overlapped manner. Either of the aAVC-NY-ESO-1 cell of the present invention or the immune checkpoint inhibitor may be administered first. In one embodiment, the administration of the aAVC-NY-ESO-1 cell of the present invention can be started prior to the administration of the immune checkpoint inhibitor. In one embodiment, the administration of the immune checkpoint inhibitor can be started prior to the administration of the aAVC-NY-ESO-1 cell of the present invention. The aAVC-NY-ESO-1 cell of the present invention and the immune checkpoint inhibitor may each independently be administered once or a plurality of times. In one embodiment, an additional anticancer agent such as a chemotherapeutic agent may be further used in combination with monotherapy or concomitant therapy of the aAVC-NY-ESO-1 cell of the present invention and the immune checkpoint inhibitor.

Particular Examples to be referred to will be provided herein for the further understanding of the present invention. However, these examples are intended for mere illustration and do not limit the present invention.

EXAMPLES

Example 1: Antitumor Effect of Mouse-Type aAVC(3T3)-NY-ESO-1 Cell

Example 1-1: Preparation of Mouse-Type aAVC(3T3)-NY-ESO-1

In order to confirm the effect as a cancer vaccine of cancer antigen NY-ESO-1-loaded aAVC in an in vivo evaluation system, mRNAs of the NY-ESO-1 gene and the CD1d gene were introduced to mouse NIH/3T3 cells (ATCC, Cat. CRL-1658) to prepare mouse-type aAVC (also referred to as aAVC(3T3)-NY-ESO-1).

The NY-ESO-1 gene (SEQ ID NO: 1) was prepared by artificial gene synthesis based on the amino acid sequence of human NY-ESO-1 set forth in SEQ ID NO: 2. The NY-ESO-1 gene was amplified by PCR using primers having an added sequence complementary to 15 nucleotides including the HindIII or EcoRI recognition sequence of pGEM(R)-4Z plasmid (Promega Corp., Cat. P2161). The amplified NY-ESO-1 gene was inserted to the HindIII-EcoRI site of pGEM(R)-4Z using In-Fusion® HD Cloning Kit (Takara Bio Inc., Cat. 639648). The obtained plasmid was designated as pGEM-4Z-NY-ESO-1 plasmid. The mouse CD1d gene (gene synthesized by artificial gene synthesis based on the amino acid sequence of UniProt: P11609-1 (SEQ ID NO: 6)) consisting of the nucleotide sequence set forth in SEQ ID NO: 5 was inserted to the HindIII-BamHI site of pGEM(R)-4Z plasmid. The obtained plasmid was designated as pGEM-4Z-mCD1d plasmid. The pGEM-4Z-NY-ESO-1 plasmid and the pGEM-4Z-mCD1d plasmid were cleaved with EcoRI and BamHI, respectively, to linearize these plasmids. NY-ESO-1 mRNA and CD1d mRNA were prepared using the resulting linearized plasmids as templates and using mMESSAGE mMACHINE™ T7 ULTRA Transcription Kit (Thermo Fisher Scientific Inc., Cat. AMB13455). NIH/3T3 cells cultured for 2 days in Dulbecco's Modified Eagle medium (Thermo Fisher Scientific Inc., Cat. 10569) containing 10% fetal bovine serum supplemented with 500 ng/mL α-GalCer were harvested. NY-ESO-1 mRNA and CD1d mRNA were added to the cell suspension, followed by electroporation (poring pulse: voltage: 150 V, pulse duration: 8 ms, pulse interval: 50 ms, the number of times: 2, decay rate: 10%, polarity: +, transfer pulse: voltage: 20 V, pulse duration: 50 ms, pulse interval: 50 ms, the number of times: ±5, decay rate: 40%, polarity: +/−) using NEPA21 electroporator (Nepa Gene Co., Ltd.). The cells were harvested and irradiated with 30 Gy of X-ray using an X-ray irradiation apparatus MBR-1520R-3 (Hitachi Power Solutions Co., Ltd.). The cells obtained by the method described above were designated as aAVC(3T3)-NY-ESO-1.

Example 1-2: Ability of aAVC(3T3)-NY-ESO-1 to Induce NY-ESO-1-Specific T Cell in Mouse $5 \times 10^5$ cells of aAVC(3T3)-NY-ESO-1 suspended in BICANATE Injection (Otsuka Pharmaceutical Co., Ltd.) were administered to the tail vein of each 6-week-old female C57BL/6J mouse (Charles River Laboratories Japan, Inc.) (n=5). 200 µL of BICANATE Injection was administered to a control group. 7 days after administration, spleen cells were recovered from the mouse, and inoculated at $4 \times 10^5$ cells/well to a plate of mouse IFN-γ single-color enzymatic ELISPOT assay kit (Cellular Technology Limited, Cat. mIFNgp-2M/5). In order to stimulate NY-ESO-1-specific T cells, NY-ESO-1 peptides (PepTivator NY-ESO-1—premium grade, human (Miltenyi Biotec, Cat. 130-095-381)) as overlapping peptides covering the full-length NY-ESO-1 protein sequence or PAP peptide (PepTivator PAP—research grade, human (Miltenyi Biotec, Cat. 130-096-767)) as antigen non-specific peptides were further added thereto, and the cells were cultured at 37° C. for 1 day under 5% $CO_2$ conditions. The number of IFN-γ-producing cells was measured by counting the number of spots on the well bottom. In the mice given aAVC(3T3)-NY-ESO-1, the number of cells producing IFN-γ was increased by NY-ESO-1 peptide stimulation (FIG. 1-1). The difference from the number of spots ascribable to antigen non-specific PAP peptide stimulation represents the number of NY-ESO-1-specific T cells. These results suggested that the administration of aAVC (3T3)-NY-ESO-1 induces NY-ESO-1-specific T cells.

Figure 2:
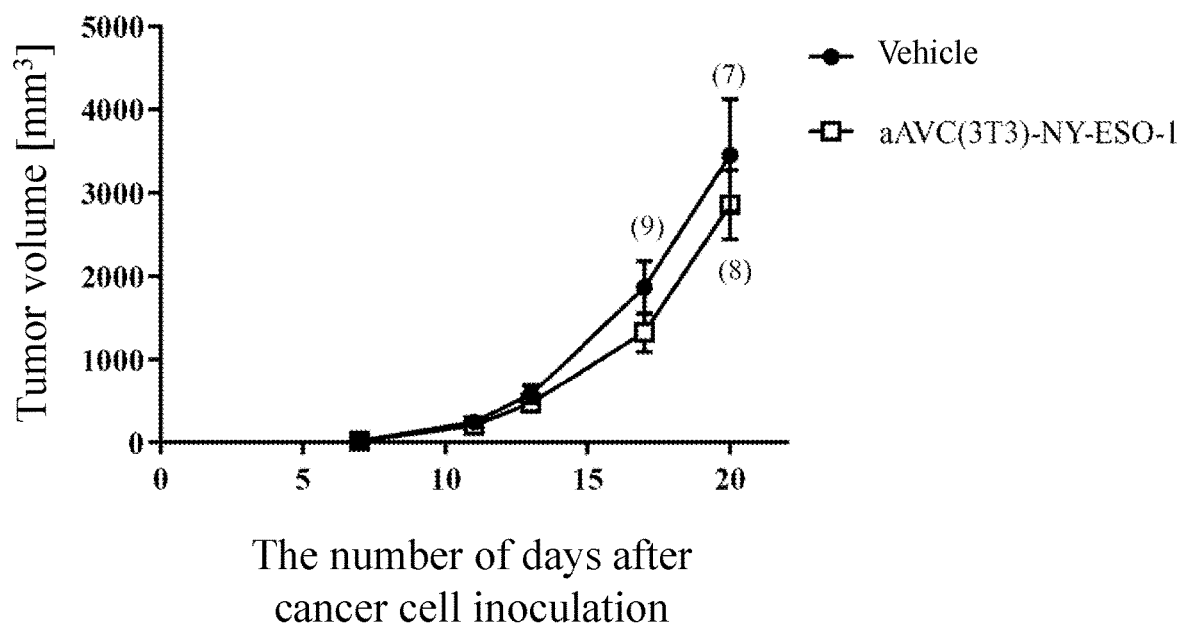

Example 1-3: Antigen-Specific Antitumor Effect of aAVC(3T3)-NY-ESO-1 in Cancer-Bearing Mouse Containing NY-ESO-1-Expressing B16 Melanoma Cell $5 \times 10^5$ cells of aAVC(3T3)-NY-ESO-1 suspended in BICANATE Injection (Otsuka Pharmaceutical Co., Ltd.) were administered to the tail vein of each 8-week-old female C57BL/6J mouse (Charles River Laboratories Japan, Inc.) (n=10 for each group). 200 μL of BICANATE Injection was administered to a control group. 14 days after administration, $3 \times 10^5$ cells of B16-F10 melanoma cells (ATCC, Cat. CRL-6475) suspended in D-PBS(−) (FUJIFILM Wako Pure Chemical Corp., Cat. 045-29795), or $3 \times 10^5$ cells of B16-F10 melanoma cells expressing the NY-ESO-1 protein (which had been prepared by the introduction of the NY-ESO-1 gene; hereinafter, referred to as B16-NY-ESO-1 or B16-NY-ESO-1 cells) suspended in D-PBS(−) were subcutaneously inoculated to the mouse. The day of inoculation of the cancer cells was set to day 0. Change in tumor volume was measured for 20 days. The administration of aAVC(3T3)-NY-ESO-1 significantly suppressed the enlargement of B16-NY-ESO-1 tumor, whereas this administration did not suppress the enlargement of B16-F10 tumor expressing no NY-ESO-1 (FIG. 1-2). These results suggested that aAVC (3T3)-NY-ESO-1 has a NY-ESO-1-specific antitumor effect based on the induction of NY-ESO-1-specific immunity.

Figures 1, 2, 3:
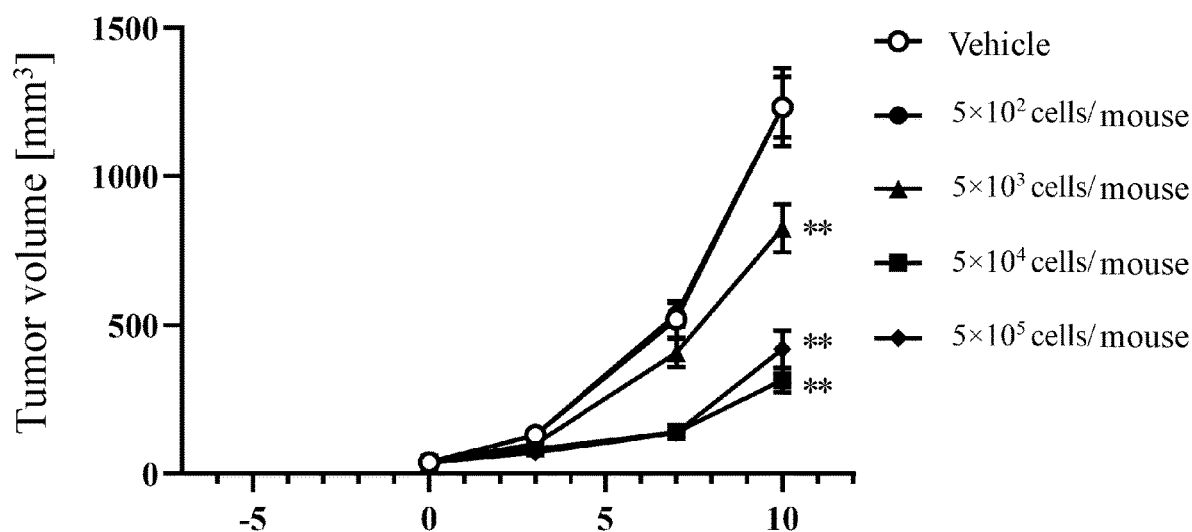

Example 1-4: Study on the Number of aAVC(3T3)-NY-ESO-1 Cells Exhibiting Antitumor Effect in NY-ESO-1-Expressing B16 Melanoma Cell Cancer-Bearing Mouse $3 \times 10^5$ cells of B16-NY-ESO-1 cells suspended in D-PBS (−) were subcutaneously inoculated to each 8-week-old C57BL/6J female mouse (Charles River Laboratories Japan, Inc.). 7 days after cell inoculation, the mice were divided into 5 groups each consisting of 10 mice on the basis of their tumor volumes. $5 \times 10^2$ cells/mouse, $5 \times 10^3$ cells/mouse, $5 \times 10^4$ cells/mouse, or $5 \times 10^5$ cells/mouse of aAVC(3T3)-NY-ESO-1 suspended in a vehicle BICANATE Injection were administered to the mice via the tail vein in each group. 200 μL of BICANATE Injection was administered to a control group. The day of administration of the aAVC(3T3)-NY-ESO-1 was set to day 0. Change in tumor volume was measured for 10 days. Since two individuals in the $5 \times 10^5$ cells/mouse administration group died after administration of aAVC(3T3)-NY-ESO-1, the number of the mice was eight for this group on day 0 or later. The progression of B16-NY-ESO-1 tumor was significantly suppressed in the $5 \times 10^3$ cells/mouse or more administration groups (FIG. 1-3). The expression level of NY-ESO-1 in aAVC(3T3)-NY-ESO-1 used in this experiment was 245 ng/$1 \times 10^6$ cells.

From the results of Example 1, the mouse-type aAVC (3T3)-NY-ESO-1 cells were confirmed to exhibit a NY-ESO-1-specific antitumor effect by inducing NY-ESO-1-specific T cells in the mouse in vivo evaluation system. In humans as well, human-type aAVC-NY-ESO-1 cells can be expected to show an antitumor effect by inducing natural immunity and also to show an antitumor effect based on acquired immunity by inducing antigen-specific acquired immunity. Therefore, studies on the preparation of human-type aAVC-NY-ESO-1 cells were made, as described below, for the purpose of developing a therapeutic drug showing a NY-ESO-1-specific antitumor effect on human NY-ESO-1-expressing cancer.[0069]

Example 2: Preparation of Human-Type aAVC-NY-ESO-1 Cell

Human-type aAVC-NY-ESO-1 cells were prepared by the following method: aAVC cells expressing NY-ESO-1, CD1d, and Tet3G were established by preparing lentiviruses using plasmids loading NY-ESO-1, CD1d, and Tet3G genes, respectively, and introducing these genes to FreeStyle 293-F cells (Thermo Fisher Scientific Inc., Cat. R79007) using the lentiviruses.

Example 2-1: Lentivirus Preparation (1) Construction of Plasmid for Lentivirus Preparation A lentivirus plasmid pLVsyn-CMV (SEQ ID NO: 7) was prepared. NY-ESO-1 gene having a 5'-terminally added EcoRI recognition sequence and a 3'-terminally added BamHI recognition sequence in NY-ESO-1 gene (SEQ ID NO: 1) was prepared by artificial gene synthesis. The NY-ESO-1 gene excised with restriction enzymes EcoRI and BamHI was inserted into the EcoRI-BamHI site of pLVsyn-CMV plasmid. The obtained plasmid was designated as pLVsyn-CMV-NY-ESO-1 plasmid. TRE3G promoter excised with restriction enzymes ClaI and EcoRI from TRE3G plasmid prepared by artificial gene synthesis service based on the sequence of pTRE3G (Takara Bio Inc., Cat. 631173) was inserted to pLVsyn-CMV-NY-ESO-1 plasmid from which CMV promoter was removed with restriction enzymes ClaI and EcoRI. The obtained plasmid was designated as pLVsyn-TRE3G-NY-ESO-1 plasmid.

The CD1d gene (SEQ ID NO: 3) was designed on the basis of the amino acid sequence of human CD1d set forth in SEQ ID NO: 4, and prepared by artificial gene synthesis by adding an XhoI recognition sequence 5'-terminally and a NotI recognition sequence 3'-terminally to the gene. The CD1d gene excised with restriction enzymes XhoI and NotI was inserted into the XhoI-NotI site of pLVsyn-CMV plasmid. The obtained plasmid was designated as pLVsyn-CMV-CD1d plasmid.

The Tet-On 3G gene was prepared by artificial gene synthesis by adding an XhoI recognition sequence 5'-terminally and a NotI recognition sequence 3'-terminally to the Tet-On 3G gene sequence of pCMV-Tet3G plasmid (Takara Bio Inc., Cat. 631335). The Tet-On 3G gene excised with restriction enzymes XhoI and NotI was inserted into the XhoI-NotI site of pLVsyn-CMV plasmid. The obtained plasmid was designated as pLVsyn-CMV-Tet3G plasmid.

(2) Lentivirus Preparation

Lentiviruses with NY-ESO-1, CD1d or Tet3G gene loaded thereon were prepared using the pLVsyn-CMV-NY-ESO-1 plasmid, the pLVsyn-TRE3G-NY-ESO-1 plasmid, the pLVsyn-CMV-CD1d plasmid, and the pLVsyn-CMV-Tet3G prepared in (1). The obtained lentiviruses were designated as CMV-NY-ESO-1-loaded lentivirus, TRE3G-NY-ESO-1-loaded lentivirus, CD1d-loaded lentivirus and Tet3G-loaded lentivirus, respectively.

6 μg of the pLVsyn-CMV-NY-ESO-1 plasmid, the pLVsyn-TRE3G-NY-ESO-1 plasmid, the pLVsyn-CMV-CD1d plasmid, or the pLVsyn-CMV-Tet3G plasmid and 18 μL of ViraPower Lentiviral Packaging Mix (Thermo Fisher Scientific Inc., Cat. K497500) were mixed, and 3 mL of OptiPRO™ SFM (Thermo Fisher Scientific Inc., Cat. 12309019) was added thereto and mixed (A). 288 µL of Lipofectamine 2000 CD Transfection Reagent (Thermo Fischer Scientific Inc., Cat. 12566-014) and 12 mL of OptiPro™ SFM were mixed and left standing for 5 minutes (B). The mixture (A) and 3 mL of the mixture (B) were mixed and left standing at room temperature for 20 minutes. Then, gene introduction was performed by adding 3 mL/plate of the mixed solution of (A) and (B) to Lenti-X™ 293T cells (Takara Bio Inc., Cat. 632180) inoculated at $5\times10^6$ cells/plate to Falcon® 100 mm TC-treated Cell Culture Dish (Corning Inc., Cat. 353003) on the previous day. The Lenti-X™ 293T cells were cultured at 37° C. under 5% $CO_2$ conditions in DMEM medium (Thermo Fisher Scientific Inc., Cat. 10569010) containing 10% fetal bovine serum (SAFC Biosciences, Cat. 12007C (γ ray-irradiated product)) and 0.1% gentamycin (Thermo Fisher Scientific Inc., Cat. 15750060). After the gene introduction, the cells were cultured for 2 days under the same conditions as above. A culture supernatant containing each gene-loaded lentivirus was recovered. The culture supernatant was centrifuged at 840×g at 4° C. for 10 minutes. The supernatant was filtered through a 0.45 µm filter (Merck KGaA, Cat. SLHV033RS), mixed with PEG-it™ Virus Precipitation Solution (5×) (System Biosciences, LLC, Cat. LV810A-1) in an amount of ¼ of the amount of the supernatant, and left standing overnight at 4° C. The mixture was centrifuged at 1500×g at 4° C. for 30 minutes for removal of a supernatant, and centrifuged again at 1500×g at 4° C. for 5 minutes to completely remove the supernatant. The pellets were suspended in 500 µL of DPBS (Thermo Fisher Scientific Inc., Cat. 14190144) to obtain CMV-NY-ESO-1-loaded lentivirus, TRE3G-NY-ESO-1-loaded lentivirus, CD1d-loaded lentivirus, and Tet3G-loaded lentivirus.

Example 2-2: Preparation and Cloning of Lentivirus-Infected Cell

FreeStyle 293-F cells were infected with each lentivirus prepared in Example 2-1. A cell population infected with the CMV-NY-ESO-1-loaded lentivirus and the CD1d-loaded lentivirus was designated as FreeStyle 293F_CMV_NY-ESO-1_CD1d cell pool. A cell population infected with the TRE3G-NY-ESO-1-loaded lentivirus, the CD1d-loaded lentivirus, and the Tet3G-loaded lentivirus was designated as FreeStyle 293F_Tet-on_NY-ESO-1_CD1d cell pool. The cloning of cells from these cell pools was carried out to obtain a plurality of clones derived from each cell pool.
(1) Preparation of FreeStyle 293F_CMV_NY-ESO-1_CD1d Cell Pool FreeStyle 293-F cells were infected with the CD1d-loaded lentivirus and the CMV-NY-ESO-1-loaded lentivirus to obtain FreeStyle 293F_CMV_NY-ESO-1 cells. Two different methods, a method of infecting the cells with the CD1d-loaded lentivirus and the CMV-NY-ESO-1-loaded lentivirus at the same time (cell pool A preparation method) or a method of infecting the cells with the CD1d-loaded lentivirus and the CMV-NY-ESO-1-loaded lentivirus sequentially (cell pool C preparation method), were used as infection methods. The FreeStyle 293-F cells were cultured in FreeStyle 293 Expression Medium (Thermo Fisher Scientific Inc., Cat. 12338018) containing 0.1% gentamycin.

The cell pool A preparation was performed by the following method: FreeStyle 293-F cells were adjusted to a concentration of $1\times10^6$ cells/mL, and inoculated in an amount of 1 mL/well to Falcon® 12-Well Flat Bottom Multiwell Cell Culture Plate with Lid (Corning Inc., Cat. 353043; hereinafter, referred to as a 12-well plate). 50 µL each or 100 µL each of the CD1d-loaded lentivirus and the CMV-NY-ESO-1-loaded lentivirus obtained in Example 2-1 was added to each well. After centrifugation at 540×g at room temperature for 30 minutes, the cells were gently suspended by pipetting, and shake-cultured. After culturing for several days, the cells thus were passaged from the 12-well plate to Corning® Polycarbonate 125 mL Erlenmeyer Flask with Vent Cap (Corning Inc., Cat. 431143; hereinafter, referred to as a 125 mL Erlenmeyer flask), and further passaged at appropriate intervals to obtain cell pool A.

The cell pool C preparation was performed by the following method: FreeStyle 293-F cells were adjusted to a concentration of $1\times10^6$ cells/mL, and inoculated in an amount of 1 mL/well to Falcon® 12-Well Flat Bottom Multiwell Cell Culture Plate with Lid. 100 µL of the CD1d-loaded lentivirus obtained in Example 2-1 was added to each well. After centrifugation at 540×g at room temperature for 30 minutes, the cells were gently suspended by pipetting, and shake-cultured. After culturing for several days, the cells thus were passaged from the 12-well plate to a 125 mL flask, and further passaged at appropriate intervals to obtain FreeStyle 293F CD1d cell pool (referred to as cell pool B). The cell pool B was passaged again to a 12-well plate. 50 µL or 200 µL of the CMV-NY-ESO-1-loaded lentivirus was added to each well. The second lentivirus infection was performed by the same procedures as in the first one. After culturing for several days, the cells thus were passaged from the 12-well plate to a 125 mL Erlenmeyer flask, and further passaged at appropriate intervals to obtain cell pool C. The cell pool A and the cell pool C were used in FreeStyle 293F_CMV_NY-ESO-1_CD1d cell pool.
(2) Preparation of FreeStyle 293F_Tet-on_NY-ESO-1_CD1d Cell Pool The cell pool B obtained during the course of the cell pool C preparation method of (1) was inoculated again to a 12-well plate. 40 µL each or 200 µL each of the TRE3G-NY-ESO-1-loaded lentivirus and the Tet3G-loaded lentivirus obtained in Example 2-1 was added to each well. Lentivirus infection was performed in accordance with the procedures described in (1). One day later, the cells were introduced from the 12-well plate to a 125 mL Erlenmeyer flask, and further passaged at appropriate intervals to obtain FreeStyle 293F_Tet-on_NY-ESO-1_CD1d cell pool.
(3) NY-ESO-1 Expression Stability and Culture Characteristics in Cell Pool Time courses of NY-ESO-1 expression levels after lentivirus infection (FIG. 2-1) and NY-ESO-1 positive rates were obtained (FIG. 2-2) as to the FreeStyle 293F_CMV_NY-ESO-1_CD1d cell pool and the FreeStyle 293F_Tet-on_NY-ESO-1_CD1d cell pool obtained in (1) and (2). The NY-ESO-1 expression was analyzed on days 3, 7, 10, and 14 after infection as to the FreeStyle 293F_CMV_NY-ESO-1_CD1d cell pool. The FreeStyle 293F_Tet-on_NY-ESO-1_CD1d cell pool was analyzed on days 7 and 14 after infection. 2 days before analysis, doxycycline (Takara Bio Inc., Cat. 631311) was added with a final concentration of 100 ng/mL to the medium to induce expression via Tet-On System. The NY-ESO-1 expression was measured by ELISA and flow cytometry. The measurement by ELISA was performed in accordance with a general measurement method of sandwich ELISA using Anti-NY-ESO-1 Antibody (Millipore Corp., Cat. MABC1151) as an antibody for immobilization, Anti-CTAG1B antibody (Abcam plc, Cat. ab183740) as a primary antibody, and Rabbit IgG Horseradish Peroxidase-conjugated Antibody (R&D Systems, Inc., Cat. HAF008) as a secondary antibody. The measurement by flow cytometry was performed in accordance with a general measurement method using Anti-NY-ESO-1 antibody as a primary antibody, APC Goat anti Mouse IgG (Life Technologies Corp., Cat. A10539) as a secondary antibody, and FACSVerse™ (BD Biosciences). At the time of passages after infection, the measurement of survival rates (FIG. 2-3) and the calculation of doubling times (FIG. 2-4) were performed as culture characteristic.

As shown as to the expression level in FIG. 2-1 and as to the positive rate in FIG. 2-2, the FreeStyle 293F_CMV_NY-ESO-1_CD1d cell pool exhibited much higher values of both the NY-ESO-1 expression level and the positive rate as compared with the FreeStyle 293F_Tet-on_NY-ESO-1_CD1d cell pool immediately after lentivirus infection, whereas decrease in expression level and positive rate was found as the number of culture days passed. On the other hand, such decrease in expression level and positive rate was not observed in the FreeStyle 293F_Tet-on_NY-ESO-1_CD1d cell pool.

Figures 1, 2:
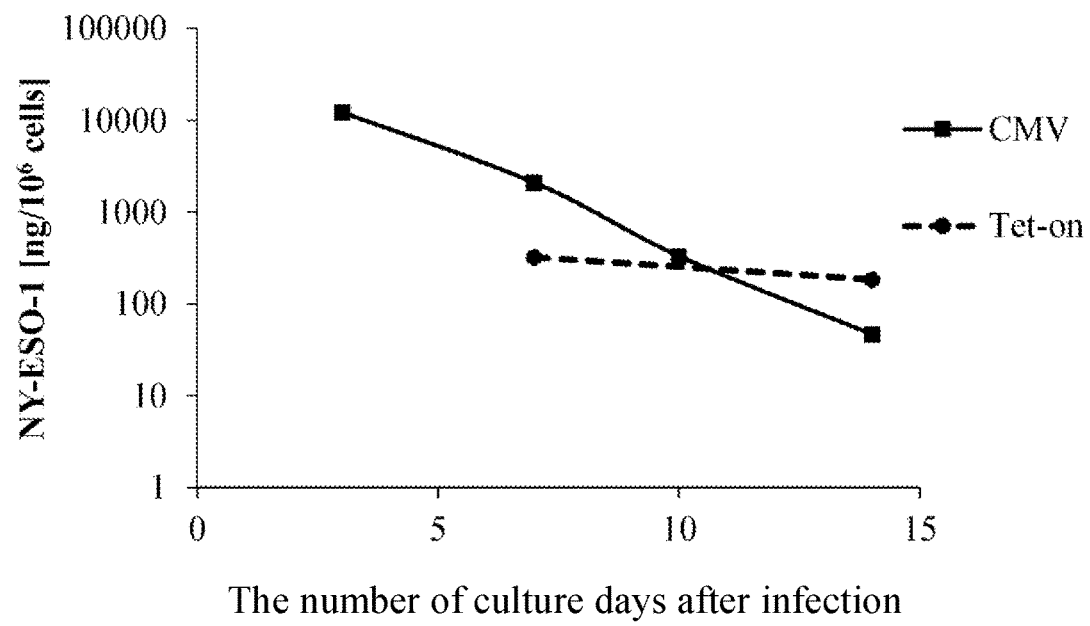
Figure 2:
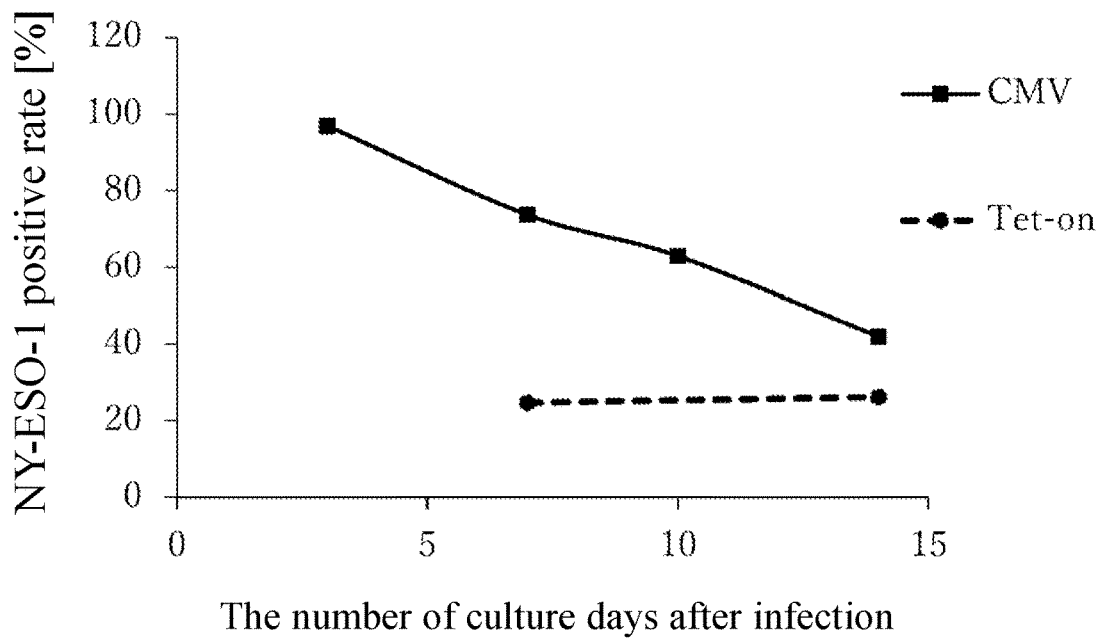
Figures 2, 3:
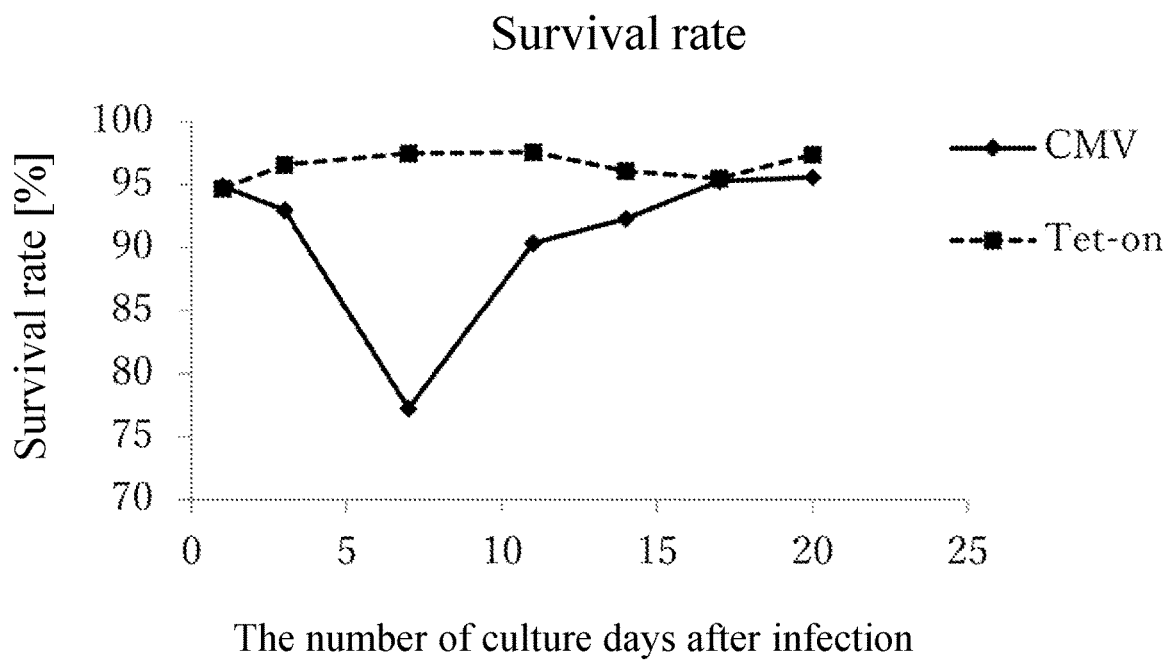
Figures 2, 3, 4:
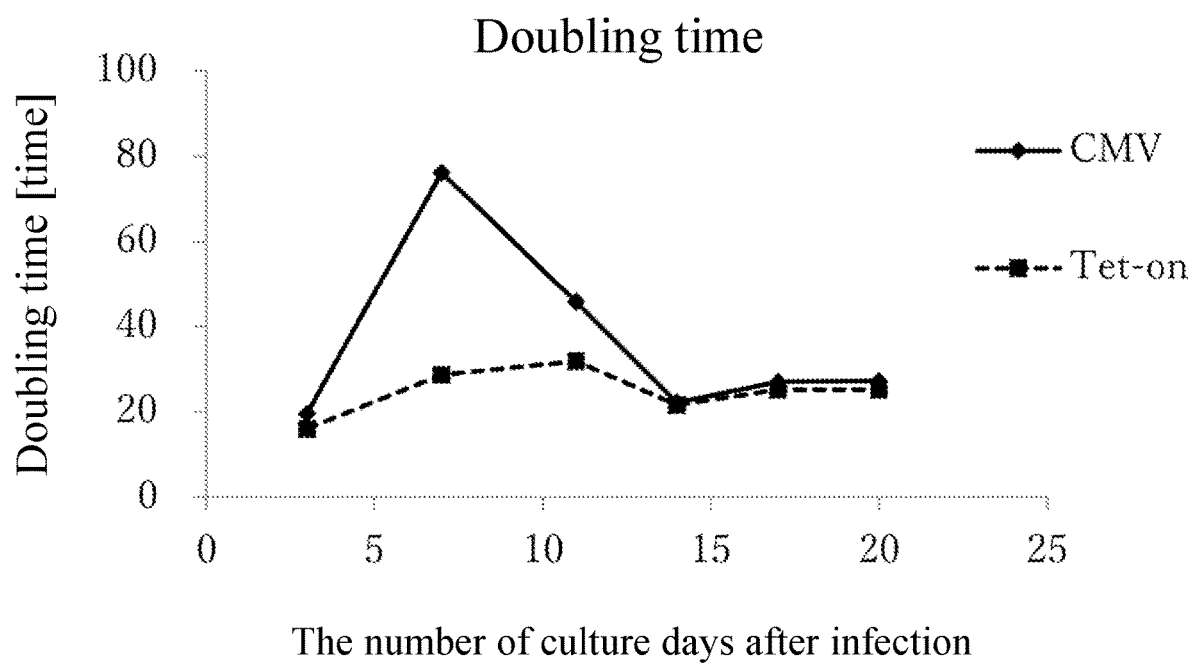
Figures 1, 4:
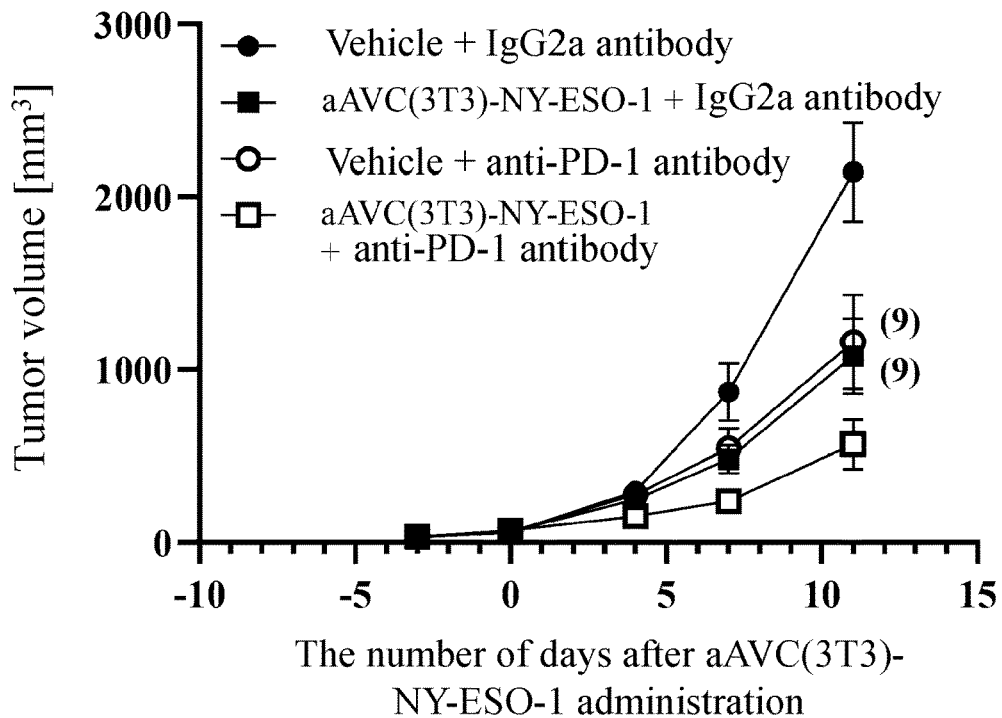
Figures 2, 4:
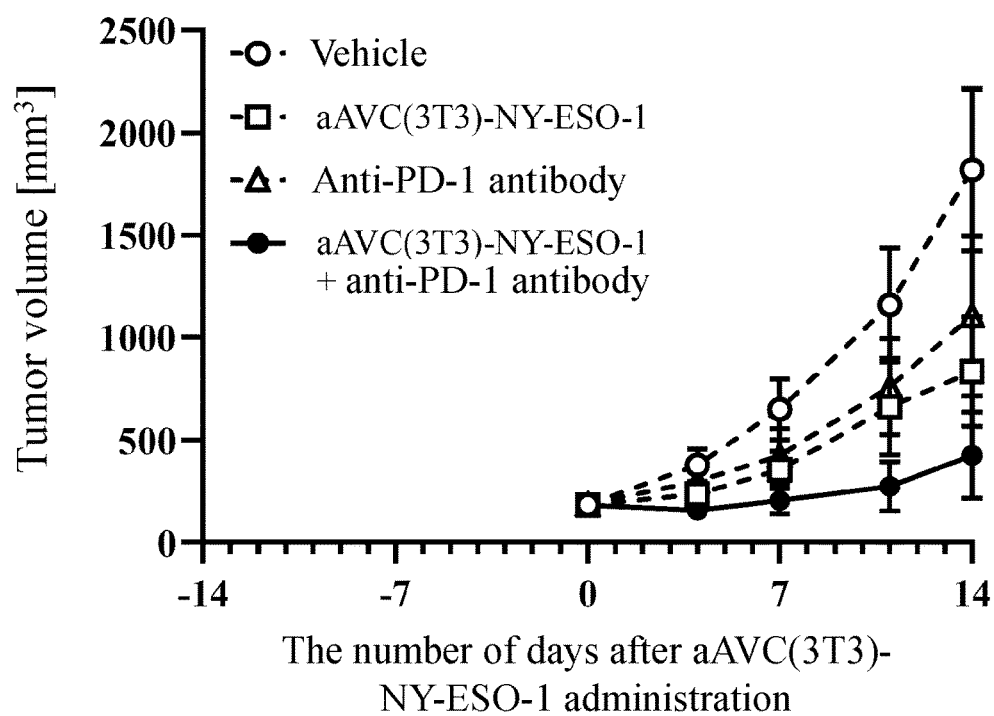

As shown as to the survival rate in FIG. 2-3 and as to the doubling time in FIG. 2-4, the FreeStyle 293F_CMV_NY-ESO-1_CD1d cell pool exhibited a decreased survival rate and a prolonged doubling time over 7 days after lentivirus infection. The total NY-ESO-1 expression level and positive rate of the cell pool were presumably decreased as the number of culture days passed, due to the prolonged doubling time associated with the decreased survival rate of cells having a high NY-ESO-1 expression level in the cell pool. On the other hand, such variations in culture characteristics were not observed in the FreeStyle 293F_Tet-on_NY-ESO-1_CD1d cell pool.

(4) Cloning

Single-cell cloning was performed by the limiting dilution method from the FreeStyle 293F_CMV_NY-ESO-1_CD1d cell pool and the FreeStyle 293F_Tet-on_NY-ESO-1_CD1d cell pool prepared in (1) and (2). Clones stably expressing all the genes were selected. The cells were inoculated at 1 cell/well to a 96-well plate and passaged according to cell proliferation so that the cells were caused to proliferate. The expression levels of the NY-ESO-1 protein and the CD1d protein in the proliferated cells were measured by ELISA for NY-ESO-1 and flow cytometry for CD1d to select clones stably expressing the NY-ESO-1 and CD1d proteins. The expression of NY-ESO-1 in the clones derived from the FreeStyle 293F_Tet-on_NY-ESO-1_CD1d cell pool was induced via Tet-On System by the addition of doxycycline with a final concentration of 100 ng/mL to the medium, and evaluated. The measurement by ELISA was performed in accordance with a general measurement method of sandwich ELISA using Anti-NY-ESO-1 Antibody as an antibody for immobilization, Anti-CTAG1B antibody as a primary antibody, and Rabbit IgG Horseradish Peroxidase-conjugated Antibody as a secondary antibody. The measurement by flow cytometry was performed in accordance with a general measurement method using APC Mouse Anti-Human CD1d antibody (BD Biosciences, Cat. 563505) and FACSVerse™ (BD Biosciences).

(5) NY-ESO-1 Expression Level of Obtained Clone

The expression level of NY-ESO-1 was measured as to the FreeStyle 293F_CMV_NY-ESO-1_CD1d cell pool-derived or FreeStyle 293F_Tet-on_NY-ESO-1_CD1d cell pool-derived clones obtained in (4). The measurement was carried out by use of the ELISA method described in (4) (FIG. 3).

As shown in FIG. 3, the expression level of NY-ESO-1 in the clones isolated from the FreeStyle 293F_CMV_NY-ESO-1_CD1d cell pool was as very low as 88 ng/$10^6$ cells at the maximum. On the other hand, the expression level of clones derived from the FreeStyle 293F_Tet-on_NY-ESO-1_CD1d cell pool differed largely therein among the clones, giving room for choice of a clone having the desired expression level. In addition, more clones than those derived from the FreeStyle 293F_CMV_NY-ESO-1_CD1d cell pool shows higher expression level.

Example 3: Effect of Combined Use of aAVC(3T3)-NY-ESO-1 and Anti-PD-1 Antibody (1) Effect of Combined Use in NY-ESO-1-Expressing B16 Melanoma Cell Cancer-Bearing Mouse $3 \times 10^5$ cells of B16-NY-ESO-1 cells suspended in D-PBS (−) were subcutaneously inoculated to each 9-week-old C57BL/6J female mouse (Charles River Laboratories Japan, Inc.). 7 days after cell inoculation, the mice were divided into 4 groups each consisting of 10 mice on the basis of their tumor volumes. 0.1 mg of an anti-PD-1 antibody (InVivoMAb anti-mouse PD-1 (CD279), Bio X Cell, Cat. BE0146) or an isotype antibody (InVivoMAb rat IgG2a isotype control, anti-trinitrophenol, Bio X Cell, Cat. BE0089) was intraperitoneally administered to the mice. The antibody was administered a total of 5 times twice a week at 3- to 4-day intervals. 3 days after the start of antibody administration, $5 \times 10^4$ cells of aAVC(3T3)-NY-ESO-1 suspended in a vehicle BICANATE Injection were administered to the tail vein of the mouse. 200 μL of BICANATE Injection was administered to a control group. The day of administration of the aAVC(3T3)-NY-ESO-1 was set to day 0. Change in tumor volume was measured up to day 11. The administration of aAVC(3T3)-NY-ESO-1+isotype antibody and the administration of the anti-PD-1 antibody suppressed the progression of B16-NY-ESO-1 tumor. The combined administration of aAVC(3T3)-NY-ESO-1 and the anti-PD-1 antibody more markedly suppressed the progression of B16-NY-ESO-1 tumor than the administration of aAVC(3T3)-NY-ESO-1+isotype antibody and the administration of the anti-PD-1 antibody (FIG. 4-1). These results suggested that combined use with an anti-PD-1 antibody enhances the antitumor effect of aAVC(3T3)-NY-ESO-1.

(2) Effect of Combined Use in NY-ESO-1-Expressing CT26 Colorectal Cancer Cell Cancer-Bearing Mouse $7 \times 10^5$ cells of NY-ESO-1 protein-expressing CT26 colorectal cancer cells (ATCC, Cat. CRL-2638) (hereinafter, referred to as CT26-NY-ESO-1 cells) prepared by the introduction of the NY-ESO-1 gene, suspended in D-PBS(−) were subcutaneously inoculated to each 7-week-old BALB/c female mouse (Charles River Laboratories Japan, Inc.). 14 days after cell inoculation, the mice were divided into 4 groups each consisting of 8 mice on the basis of their tumor volumes. 0.1 mg of an anti-PD-1 antibody was intraperitoneally administered to the mouse. No antibody was administered to an antibody non-administration group. The antibody was administered a total of 4 times twice a week at 3- to 4-day intervals. On the start day of antibody administration, $5 \times 10^5$ cells of aAVC(3T3)-NY-ESO-1 suspended in a vehicle BICANATE Injection were administered to the tail vein of the mouse. 200 μL of BICANATE Injection was administered to a control group. The day of administration of the aAVC(3T3)-NY-ESO-1 was set to day 0. Change in tumor volume was measured up to day 14. The administration of aAVC(3T3)-NY-ESO-1 alone and the administration of the anti-PD-1 antibody alone suppressed the progression of CT26-NY-ESO-1 tumor, whereas the combined use of aAVC(3T3)-NY-ESO-1 administration and the anti-PD-1 antibody more markedly suppressed the progression of CT26-NY-ESO-1 than the administration of each agent alone (FIG. 4-2). These results suggested that combined use with an anti-PD-1 antibody enhances the antitumor effect of aAVC(3T3)-NY-ESO-1.

Figure 5:
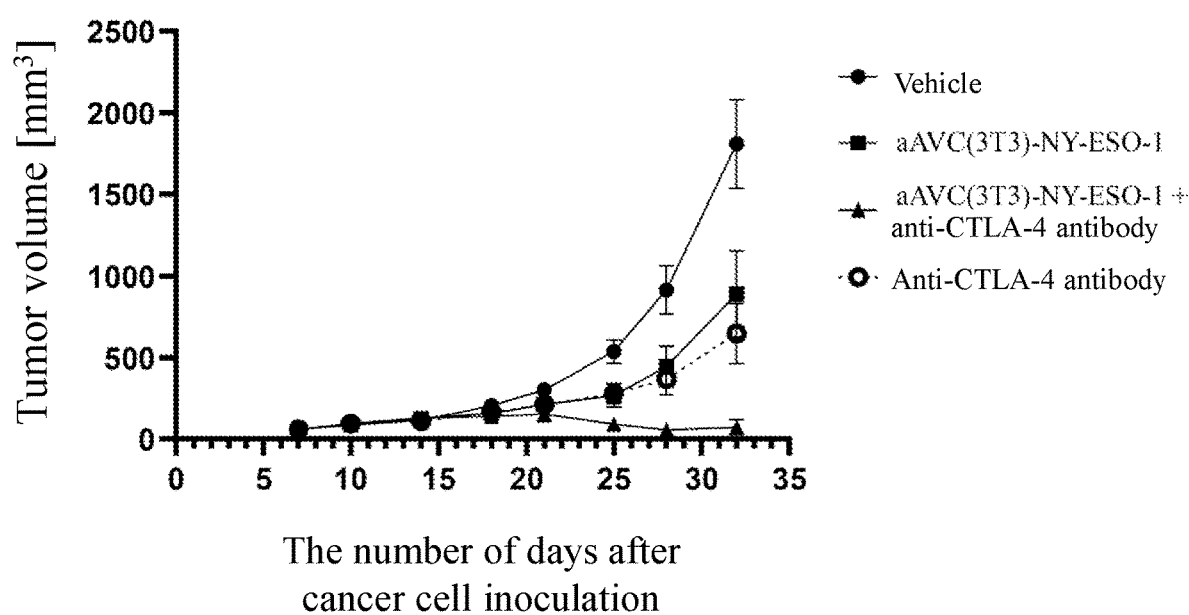
FIG. 5 shows the antitumor effects of aAVC(3T3)-NY-ESO-1 cells, an anti-CTLA-4 antibody and combined use thereof in NY-ESO-1-expressing CT26 cancer-bearing mice. The ordinate depicts a tumor volume, and the abscissa depicts the number of days after cancer cell inoculation. The vertical lines depict mean±standard error. n=9 for the aAVC (3T3)-NY-ESO-1 cells and anti-CTLA-4 antibody combined use group on day 18 or later.

Example 4: Effect of Combined Use of aAVC(3T3)-NY-ESO-1 and Anti-CTLA-4 Antibody $7 \times 10^5$ cells of CT26-NY-ESO-1 cells suspended in D-PBS(−) were subcutaneously inoculated to each 7-week-old BALB/c female mouse (Charles River Laboratories Japan, Inc.). 7 days after cell inoculation, the mice were divided into 4 groups each consisting of 10 mice on the basis of their tumor volumes. 7 days after grouping, 0.15 mg of an anti-CTLA-4 antibody (InVivoMAb anti-mouse CTLA-4 (CD152), Bio X Cell, Cat. BE0164) was intraperitoneally administered to the mouse. No antibody was administered to an antibody non-administration group. The antibody was administered a total of 5 times twice a week at 3- to 4-day intervals. On the start day of antibody administration, $5 \times 10^5$ cells of aAVC(3T3)-NY-ESO-1 suspended in a vehicle BICANATE Injection were administered to the tail vein of the mouse. One individual in the combined use group of AVC(3T3)-NY-ESO-1 cell+anti-CTLA-4 antibody died after administration of aAVC(3T3)-NY-ESO-1. 200 μL of BICANATE Injection was administered to a control group. The day of inoculation of the cancer cells was set to day 0. Change in tumor volume was measured for 32 days. The administration of aAVC(3T3)-NY-ESO-1 alone and the administration of the anti-CTLA-4 antibody alone suppressed the progression of CT26-NY-ESO-1 tumor, whereas the combined use of aAVC(3T3)-NY-ESO-1 and the anti-CTLA-4 antibody more markedly suppressed the progression of CT26-NY-ESO-1 than the administration of each agent alone (FIG. 5). These results suggested that combined use with an anti-CTLA-4 antibody enhances the antitumor effect of aAVC(3T3)-NY-ESO-1.

INDUSTRIAL APPLICABILITY

The aAVC-NY-ESO-1 cell of the present invention can be expected to be useful in treating a cancer.

Free Text of Sequence Listing

The nucleotide sequence set forth in SEQ ID NO: 1 of the sequence listing is a nucleotide sequence encoding human NY-ESO-1 protein, and the amino acid sequence set forth in SEQ ID NO: 2 of the sequence listing is an amino acid sequence encoded by the sequence of SEQ ID NO: 1. The nucleotide sequence set forth in SEQ ID NO: 3 of the sequence listing is a nucleotide sequence encoding human CD1d protein, and the amino acid sequence set forth in SEQ ID NO: 4 of the sequence listing is an amino acid sequence encoded by the sequence of SEQ ID NO: 3. The nucleotide sequence set forth in SEQ ID NO: 5 of the sequence listing is a nucleotide sequence encoding mouse CD1d protein, and the amino acid sequence set forth in SEQ ID NO: 6 of the sequence listing is an amino acid sequence encoded by the sequence of SEQ ID NO: 5. The nucleotide sequence set forth in SEQ ID NO: 7 of the sequence listing is the nucleotide sequence of pLVsyn-CMV. These sequences are as described in the description of "Artificial Sequence" in the numeric caption <223> of the sequence listing given below.

What is claimed is:

1. A method for treating a cancer in a subject, comprising administering to the subject a cell comprising a polynucleotide encoding human CD1d and a polynucleotide encoding human NY-ESO-1 or a fragment thereof,
   wherein the polynucleotide encoding NY-ESO-1 or a fragment thereof is operably linked to a tetracycline-inducible promoter,
   wherein the cell is cultured in vitro in the presence of a tetracycline to express human CD1d and human NY-ESO-1 or a fragment thereof,
   wherein an expression level of the NY-ESO-1 or the fragment thereof is 245 ng to 45000 ng per $10^6$ cells,
   wherein a CD1d ligand is loaded on the surface of the cell,
   wherein the CD1d ligand is α-GalCer, and
   wherein the cell is derived from a human embryonic kidney cell.

2. The method of claim 1, further comprising administering an immune checkpoint inhibitor to the subject.

3. The method according to claim 2, wherein the immune checkpoint inhibitor is a PD-1 immune checkpoint inhibitor or a CTLA-4 immune checkpoint inhibitor.

4. The method according to claim 1, wherein the human embryonic kidney cell is a human embryonic kidney cell 293 (HEK293) cell.

* * * * *

SEQUENCE LISTING

```
<160> NUMBER OF SEQ ID NOS: 7

<210> SEQ ID NO 1
<211> LENGTH: 543
<212> TYPE: DNA
<213> ORGANISM: Homo sapiens
<220> FEATURE:
<221> NAME/KEY: CDS
<222> LOCATION: (1)..(540)

<400> SEQUENCE: 1 atg cag gcc gag ggc aga ggc aca ggc gga tct act ggg gat gct gat         48
Met Gln Ala Glu Gly Arg Gly Thr Gly Gly Ser Thr Gly Asp Ala Asp
1               5                   10                  15 gga cct ggc ggc cct ggc att cca gat ggc cca ggc gga aat gct ggc         96
Gly Pro Gly Gly Pro Gly Ile Pro Asp Gly Pro Gly Gly Asn Ala Gly
            20                  25                  30 gga cca ggc gaa gct ggc gct aca ggc gga aga gga cct aga ggc gct        144
Gly Pro Gly Glu Ala Gly Ala Thr Gly Gly Arg Gly Pro Arg Gly Ala
        35                  40                  45 ggc gcc gct aga gct tct gga cct ggg gga ggc gct cct aga gga cct        192
Gly Ala Ala Arg Ala Ser Gly Pro Gly Gly Gly Ala Pro Arg Gly Pro
    50                  55                  60 cat ggc gga gct gcc tct ggc ctg aat ggc tgc tgt aga tgt ggc gcc        240
His Gly Gly Ala Ala Ser Gly Leu Asn Gly Cys Cys Arg Cys Gly Ala
65                  70                  75                  80 aga ggc ccc gaa agc cgg ctg ctg gag ttt tac ctg gcc atg ccc ttc        288
Arg Gly Pro Glu Ser Arg Leu Leu Glu Phe Tyr Leu Ala Met Pro Phe
                85                  90                  95
```

```
gcc acc ccc atg gaa gct gag ctg gcc aga aga agc ctg gcc cag gac     336
Ala Thr Pro Met Glu Ala Glu Leu Ala Arg Arg Ser Leu Ala Gln Asp
            100                 105                 110 gct cct cca ctg cct gtg cca ggc gtg ctg ctg aaa gag ttc acc gtg     384
Ala Pro Pro Leu Pro Val Pro Gly Val Leu Leu Lys Glu Phe Thr Val
        115                 120                 125 tcc ggc aac atc ctg acc atc cgg ctg aca gcc gcc gac cac aga cag     432
Ser Gly Asn Ile Leu Thr Ile Arg Leu Thr Ala Ala Asp His Arg Gln
130                 135                 140 ctg cag ctg agc atc agc agc tgc ctg cag cag ctg tcc ctg ctg atg     480
Leu Gln Leu Ser Ile Ser Ser Cys Leu Gln Gln Leu Ser Leu Leu Met
145                 150                 155                 160 tgg atc acc cag tgc ttt ctg ccc gtg ttt ctg gcc cag cct cct agc     528
Trp Ile Thr Gln Cys Phe Leu Pro Val Phe Leu Ala Gln Pro Pro Ser
                165                 170                 175 ggc cag cgg aga taa                                                 543
Gly Gln Arg Arg
        180
```

<210> SEQ ID NO 2
<211> LENGTH: 180
<212> TYPE: PRT
<213> ORGANISM: Homo sapiens

<400> SEQUENCE: 2

```
Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
        180
```

<210> SEQ ID NO 3
<211> LENGTH: 1008
<212> TYPE: DNA
<213> ORGANISM: Homo sapiens
<220> FEATURE:
<221> NAME/KEY: CDS
<222> LOCATION: (1)..(1005)

<400> SEQUENCE: 3

```
atg ggc tgc ctg ctg ttt ctg ctg ctg tgg gcc ctg ctg cag gcc tgg      48
Met Gly Cys Leu Leu Phe Leu Leu Leu Trp Ala Leu Leu Gln Ala Trp
1               5                   10                  15 gga tct gct gaa gtg ccc cag aga ctg ttc ccc ctg cgg tgc ctg cag      96
Gly Ser Ala Glu Val Pro Gln Arg Leu Phe Pro Leu Arg Cys Leu Gln
            20                  25                  30 atc agc agc ttc gcc aac agc agc tgg acc aga acc gat ggc ctg gcc     144
Ile Ser Ser Phe Ala Asn Ser Ser Trp Thr Arg Thr Asp Gly Leu Ala
        35                  40                  45 tgg ctg gga gag ctg cag aca cac agc tgg tcc aac gac agc gac acc     192
Trp Leu Gly Glu Leu Gln Thr His Ser Trp Ser Asn Asp Ser Asp Thr
50                  55                  60 gtg cgg agc ctg aag cct tgg agc cag ggc acc ttt agc gac cag cag     240
Val Arg Ser Leu Lys Pro Trp Ser Gln Gly Thr Phe Ser Asp Gln Gln
65                  70                  75                  80 tgg gag aca ctg cag cac atc ttc cgg gtg tac aga agc agc ttc acc     288
Trp Glu Thr Leu Gln His Ile Phe Arg Val Tyr Arg Ser Ser Phe Thr
                85                  90                  95 cgg gac gtg aaa gaa ttt gcc aag atg ctg cgg ctg agc tac ccc ctg     336
Arg Asp Val Lys Glu Phe Ala Lys Met Leu Arg Leu Ser Tyr Pro Leu
            100                 105                 110 gaa ctg cag gtg tcc gcc ggc tgt gaa gtg cac cct ggc aac gcc agc     384
Glu Leu Gln Val Ser Ala Gly Cys Glu Val His Pro Gly Asn Ala Ser
        115                 120                 125 aac aac ttc ttc cac gtg gcc ttc cag ggc aag gac ata ctg agc ttt     432
Asn Asn Phe Phe His Val Ala Phe Gln Gly Lys Asp Ile Leu Ser Phe
130                 135                 140 cag ggc acc agc tgg gag ccc aca cag gaa gct cca ctg tgg gtc aac     480
Gln Gly Thr Ser Trp Glu Pro Thr Gln Glu Ala Pro Leu Trp Val Asn
145                 150                 155                 160 ctg gcc atc cag gtg ctg aac cag gac aag tgg acc cgg gaa acc gtg     528
Leu Ala Ile Gln Val Leu Asn Gln Asp Lys Trp Thr Arg Glu Thr Val
                165                 170                 175 cag tgg ctg ctg aac ggc acc tgt ccc cag ttt gtg tcc ggc ctg ctg     576
Gln Trp Leu Leu Asn Gly Thr Cys Pro Gln Phe Val Ser Gly Leu Leu
            180                 185                 190 gaa agc ggc aag agc gag ctg aag aaa caa gtg aag ccc aaa gcc tgg     624
Glu Ser Gly Lys Ser Glu Leu Lys Lys Gln Val Lys Pro Lys Ala Trp
        195                 200                 205 ctg agc aga ggc cct tct cct gga cct gga cgg ctg ctc ctc gtg tgt     672
Leu Ser Arg Gly Pro Ser Pro Gly Pro Gly Arg Leu Leu Leu Val Cys
210                 215                 220 cac gtg tcc ggc ttc tac ccc aag ccc gtg tgg gtc aag tgg atg cgg     720
His Val Ser Gly Phe Tyr Pro Lys Pro Val Trp Val Lys Trp Met Arg
225                 230                 235                 240 gga gaa cag gaa cag cag ggc acc cag cct ggc gac atc ctg cct aac     768
Gly Glu Gln Glu Gln Gln Gly Thr Gln Pro Gly Asp Ile Leu Pro Asn
                245                 250                 255 gcc gac gag aca tgg tat ctg cgg gcc acc ctg gat gtg gtg gct ggc     816
Ala Asp Glu Thr Trp Tyr Leu Arg Ala Thr Leu Asp Val Val Ala Gly
            260                 265                 270 gaa gca gcc ggc ctg tcc tgt aga gtg aag cac agc agc ctg gaa gga     864
Glu Ala Ala Gly Leu Ser Cys Arg Val Lys His Ser Ser Leu Glu Gly
        275                 280                 285 cag gac atc gtg ctg tac tgg ggc ggc agc tac acc agc atg gga ctg     912
Gln Asp Ile Val Leu Tyr Trp Gly Gly Ser Tyr Thr Ser Met Gly Leu
290                 295                 300
```

| | | | | | | | | | | | | |
|---|---|---|---|---|---|---|---|---|---|---|---|---|
| att | gct | ctg | gcc | gtg | ctg | gcc | tgt | ctg | ctg | ttt | ctg | ctg | atc | gtg | gga | | 960 |
| Ile | Ala | Leu | Ala | Val | Leu | Ala | Cys | Leu | Leu | Phe | Leu | Leu | Ile | Val | Gly | | |
| 305 | | | | 310 | | | | | 315 | | | | | 320 | | | |

| | | | | | | | | | | | |
|---|---|---|---|---|---|---|---|---|---|---|---|
| ttc | acc | agc | cgg | ttc | aag | cgg | cag | acc | agc | tac | cag | ggc | gtg | ctc | tga | 1008 |
| Phe | Thr | Ser | Arg | Phe | Lys | Arg | Gln | Thr | Ser | Tyr | Gln | Gly | Val | Leu | | |
| | | | | 325 | | | | | 330 | | | | | 335 | | |

<210> SEQ ID NO 4
<211> LENGTH: 335
<212> TYPE: PRT
<213> ORGANISM: Homo sapiens

<400> SEQUENCE: 4

Met Gly Cys Leu Leu Phe Leu Leu Leu Trp Ala Leu Leu Gln Ala Trp
1               5                   10                  15

Gly Ser Ala Glu Val Pro Gln Arg Leu Phe Pro Leu Arg Cys Leu Gln
            20                  25                  30

Ile Ser Ser Phe Ala Asn Ser Ser Trp Thr Arg Thr Asp Gly Leu Ala
        35                  40                  45

Trp Leu Gly Glu Leu Gln Thr His Ser Trp Ser Asn Asp Ser Asp Thr
    50                  55                  60

Val Arg Ser Leu Lys Pro Trp Ser Gln Gly Thr Phe Ser Asp Gln Gln
65                  70                  75                  80

Trp Glu Thr Leu Gln His Ile Phe Arg Val Tyr Arg Ser Ser Phe Thr
                85                  90                  95

Arg Asp Val Lys Glu Phe Ala Lys Met Leu Arg Leu Ser Tyr Pro Leu
            100                 105                 110

Glu Leu Gln Val Ser Ala Gly Cys Glu Val His Pro Gly Asn Ala Ser
        115                 120                 125

Asn Asn Phe Phe His Val Ala Phe Gln Gly Lys Asp Ile Leu Ser Phe
    130                 135                 140

Gln Gly Thr Ser Trp Glu Pro Thr Gln Glu Ala Pro Leu Trp Val Asn
145                 150                 155                 160

Leu Ala Ile Gln Val Leu Asn Gln Asp Lys Trp Thr Arg Glu Thr Val
                165                 170                 175

Gln Trp Leu Leu Asn Gly Thr Cys Pro Gln Phe Val Ser Gly Leu Leu
            180                 185                 190

Glu Ser Gly Lys Ser Glu Leu Lys Lys Gln Val Lys Pro Lys Ala Trp
        195                 200                 205

Leu Ser Arg Gly Pro Ser Pro Gly Pro Gly Arg Leu Leu Leu Val Cys
    210                 215                 220

His Val Ser Gly Phe Tyr Pro Lys Pro Val Trp Val Lys Trp Met Arg
225                 230                 235                 240

Gly Glu Gln Glu Gln Gln Gly Thr Gln Pro Gly Asp Ile Leu Pro Asn
                245                 250                 255

Ala Asp Glu Thr Trp Tyr Leu Arg Ala Thr Leu Asp Val Val Ala Gly
            260                 265                 270

Glu Ala Ala Gly Leu Ser Cys Arg Val Lys His Ser Ser Leu Glu Gly
        275                 280                 285

Gln Asp Ile Val Leu Tyr Trp Gly Gly Ser Tyr Thr Ser Met Gly Leu
    290                 295                 300

Ile Ala Leu Ala Val Leu Ala Cys Leu Leu Phe Leu Leu Ile Val Gly
305                 310                 315                 320

Phe Thr Ser Arg Phe Lys Arg Gln Thr Ser Tyr Gln Gly Val Leu
                325                 330                 335

```
<210> SEQ ID NO 5
<211> LENGTH: 1011
<212> TYPE: DNA
<213> ORGANISM: Mus musculus
<220> FEATURE:
<221> NAME/KEY: CDS
<222> LOCATION: (1)..(1008)

<400> SEQUENCE: 5
```

| | | | | | | | | | | | | | | | | |
|---|---|---|---|---|---|---|---|---|---|---|---|---|---|---|---|---|
| atg | aga | tac | ctg | ccc | tgg | ctg | ctg | ctg | tgg | gcc | ttc | ctc | cag | gtg | tgg | 48 |
| Met | Arg | Tyr | Leu | Pro | Trp | Leu | Leu | Leu | Trp | Ala | Phe | Leu | Gln | Val | Trp | |
| 1 | | | | 5 | | | | | 10 | | | | | 15 | | |
| gga | cag | tct | gag | gcc | cag | cag | aag | aac | tac | acc | ttc | cgg | tgc | ctg | cag | 96 |
| Gly | Gln | Ser | Glu | Ala | Gln | Gln | Lys | Asn | Tyr | Thr | Phe | Arg | Cys | Leu | Gln | |
| | | | 20 | | | | | 25 | | | | | 30 | | | |
| atg | agc | agc | ttc | gcc | aac | aga | agc | tgg | tcc | cgg | acc | gac | agc | gtc | gtg | 144 |
| Met | Ser | Ser | Phe | Ala | Asn | Arg | Ser | Trp | Ser | Arg | Thr | Asp | Ser | Val | Val | |
| | | 35 | | | | | 40 | | | | | 45 | | | | |
| tgg | ctg | gga | gat | ctg | cag | acc | cac | aga | tgg | tcc | aac | gac | agc | gcc | acc | 192 |
| Trp | Leu | Gly | Asp | Leu | Gln | Thr | His | Arg | Trp | Ser | Asn | Asp | Ser | Ala | Thr | |
| | 50 | | | | | 55 | | | | | 60 | | | | | |
| atc | agc | ttc | acc | aag | ccc | tgg | tcc | cag | ggc | aag | ctg | agc | aac | cag | cag | 240 |
| Ile | Ser | Phe | Thr | Lys | Pro | Trp | Ser | Gln | Gly | Lys | Leu | Ser | Asn | Gln | Gln | |
| 65 | | | | | 70 | | | | | 75 | | | | | 80 | |
| tgg | gag | aag | ctg | cag | cac | atg | ttc | cag | gtg | tac | cgg | gtg | tcc | ttc | acc | 288 |
| Trp | Glu | Lys | Leu | Gln | His | Met | Phe | Gln | Val | Tyr | Arg | Val | Ser | Phe | Thr | |
| | | | | 85 | | | | | 90 | | | | | 95 | | |
| cgg | gac | atc | cag | gaa | ctc | gtg | aag | atg | atg | agc | ccc | aaa | gag | gac | tac | 336 |
| Arg | Asp | Ile | Gln | Glu | Leu | Val | Lys | Met | Met | Ser | Pro | Lys | Glu | Asp | Tyr | |
| | | | 100 | | | | | 105 | | | | | 110 | | | |
| ccc | atc | gag | atc | cag | ctg | agc | gcc | ggc | tgc | gag | atg | tac | cct | ggc | aat | 384 |
| Pro | Ile | Glu | Ile | Gln | Leu | Ser | Ala | Gly | Cys | Glu | Met | Tyr | Pro | Gly | Asn | |
| | | 115 | | | | | 120 | | | | | 125 | | | | |
| gcc | agc | gag | agc | ttc | ctg | cac | gtg | gcc | ttc | cag | ggc | aaa | tac | gtc | gtg | 432 |
| Ala | Ser | Glu | Ser | Phe | Leu | His | Val | Ala | Phe | Gln | Gly | Lys | Tyr | Val | Val | |
| | 130 | | | | | 135 | | | | | 140 | | | | | |
| cgg | ttc | tgg | ggc | acc | agc | tgg | cag | aca | gtg | cct | ggc | gct | cct | agc | tgg | 480 |
| Arg | Phe | Trp | Gly | Thr | Ser | Trp | Gln | Thr | Val | Pro | Gly | Ala | Pro | Ser | Trp | |
| 145 | | | | | 150 | | | | | 155 | | | | | 160 | |
| ctg | gac | ctg | cct | atc | aag | gtg | ctg | aac | gcc | gac | cag | ggc | aca | agc | gcc | 528 |
| Leu | Asp | Leu | Pro | Ile | Lys | Val | Leu | Asn | Ala | Asp | Gln | Gly | Thr | Ser | Ala | |
| | | | | 165 | | | | | 170 | | | | | 175 | | |
| aca | gtg | cag | atg | ctg | ctg | aac | gac | aca | tgc | ccc | ctg | ttc | gtg | cgg | gga | 576 |
| Thr | Val | Gln | Met | Leu | Leu | Asn | Asp | Thr | Cys | Pro | Leu | Phe | Val | Arg | Gly | |
| | | | 180 | | | | | 185 | | | | | 190 | | | |
| ctg | ctg | gaa | gcc | ggc | aag | agc | gac | ctg | gaa | aag | cag | gaa | aag | ccc | gtg | 624 |
| Leu | Leu | Glu | Ala | Gly | Lys | Ser | Asp | Leu | Glu | Lys | Gln | Glu | Lys | Pro | Val | |
| | | 195 | | | | | 200 | | | | | 205 | | | | |
| gcc | tgg | ctg | agc | agc | gtg | cca | tct | tct | gcc | gat | ggc | cac | aga | cag | ctc | 672 |
| Ala | Trp | Leu | Ser | Ser | Val | Pro | Ser | Ser | Ala | Asp | Gly | His | Arg | Gln | Leu | |
| | 210 | | | | | 215 | | | | | 220 | | | | | |
| gtg | tgc | cac | gtg | tcc | ggc | ttc | tac | ccc | aag | ccc | gtg | tgg | gtc | atg | tgg | 720 |
| Val | Cys | His | Val | Ser | Gly | Phe | Tyr | Pro | Lys | Pro | Val | Trp | Val | Met | Trp | |
| 225 | | | | | 230 | | | | | 235 | | | | | 240 | |
| atg | cgg | ggc | gac | cag | gaa | cag | cag | ggc | aca | cac | aga | ggc | gac | ttt | ctg | 768 |
| Met | Arg | Gly | Asp | Gln | Glu | Gln | Gln | Gly | Thr | His | Arg | Gly | Asp | Phe | Leu | |
| | | | | 245 | | | | | 250 | | | | | 255 | | |
| ccc | aac | gcc | gac | gag | aca | tgg | tat | ctg | caa | gcc | acc | ctg | gac | gtg | gaa | 816 |
| Pro | Asn | Ala | Asp | Glu | Thr | Trp | Tyr | Leu | Gln | Ala | Thr | Leu | Asp | Val | Glu | |
| | | | 260 | | | | | 265 | | | | | 270 | | | |

| | | | | | | | | | | | | | | | | |
|---|---|---|---|---|---|---|---|---|---|---|---|---|---|---|---|---|
|gct|ggc|gag|gaa|gct|gga|ctg|gcc|tgc|aga|gtg|aag|cac|agc|tct|ctg|864|
|Ala|Gly|Glu|Glu|Ala|Gly|Leu|Ala|Cys|Arg|Val|Lys|His|Ser|Ser|Leu| |
| | |275| | | |280| | | |285| | | | | | |
|ggc|ggc|cag|gac|atc|atc|ctg|tac|tgg|gat|gcc|aga|cag|gcc|cca|gtg|912|
|Gly|Gly|Gln|Asp|Ile|Ile|Leu|Tyr|Trp|Asp|Ala|Arg|Gln|Ala|Pro|Val| |
| |290| | | |295| | | |300| | | | | | | |
|ggc|ctg|atc|gtg|ttc|atc|gtg|ctg|atc|atg|ctg|gtg|gtc|gtg|ggc|gcc|960|
|Gly|Leu|Ile|Val|Phe|Ile|Val|Leu|Ile|Met|Leu|Val|Val|Val|Gly|Ala| |
|305| | | | |310| | | |315| | | | |320| | |
|gtg|gtg|tac|tac|atc|tgg|cgg|aga|aga|agc|gcc|tac|cag|gat|atc|aga|1008|
|Val|Val|Tyr|Tyr|Ile|Trp|Arg|Arg|Arg|Ser|Ala|Tyr|Gln|Asp|Ile|Arg| |
| | | | |325| | | |330| | | | |335| | | |
|tga| | | | | | | | | | | | | | | |1011|

<210> SEQ ID NO 6
<211> LENGTH: 336
<212> TYPE: PRT
<213> ORGANISM: Mus musculus

<400> SEQUENCE: 6

Met Arg Tyr Leu Pro Trp Leu Leu Leu Trp Ala Phe Leu Gln Val Trp
1               5                   10                  15

Gly Gln Ser Glu Ala Gln Lys Asn Tyr Thr Phe Arg Cys Leu Gln
            20                  25                  30

Met Ser Ser Phe Ala Asn Arg Ser Trp Ser Arg Thr Asp Ser Val Val
        35                  40                  45

Trp Leu Gly Asp Leu Gln Thr His Arg Trp Ser Asn Asp Ser Ala Thr
    50                  55                  60

Ile Ser Phe Thr Lys Pro Trp Ser Gln Gly Lys Leu Ser Asn Gln Gln
65                  70                  75                  80

Trp Glu Lys Leu Gln His Met Phe Gln Val Tyr Arg Val Ser Phe Thr
                85                  90                  95

Arg Asp Ile Gln Glu Leu Val Lys Met Met Ser Pro Lys Glu Asp Tyr
            100                 105                 110

Pro Ile Glu Ile Gln Leu Ser Ala Gly Cys Glu Met Tyr Pro Gly Asn
        115                 120                 125

Ala Ser Glu Ser Phe Leu His Val Ala Phe Gln Gly Lys Tyr Val Val
    130                 135                 140

Arg Phe Trp Gly Thr Ser Trp Gln Thr Val Pro Gly Ala Pro Ser Trp
145                 150                 155                 160

Leu Asp Leu Pro Ile Lys Val Leu Asn Ala Asp Gln Gly Thr Ser Ala
                165                 170                 175

Thr Val Gln Met Leu Leu Asn Asp Thr Cys Pro Leu Phe Val Arg Gly
            180                 185                 190

Leu Leu Glu Ala Gly Lys Ser Asp Leu Glu Lys Gln Glu Lys Pro Val
        195                 200                 205

Ala Trp Leu Ser Ser Val Pro Ser Ser Ala Asp Gly His Arg Gln Leu
    210                 215                 220

Val Cys His Val Ser Gly Phe Tyr Pro Lys Pro Val Trp Val Met Trp
225                 230                 235                 240

Met Arg Gly Asp Gln Glu Gln Gln Gly Thr His Arg Gly Asp Phe Leu
                245                 250                 255

Pro Asn Ala Asp Glu Thr Trp Tyr Leu Gln Ala Thr Leu Asp Val Glu
            260                 265                 270

Ala Gly Glu Glu Ala Gly Leu Ala Cys Arg Val Lys His Ser Ser Leu
        275                 280                 285

| | | | |
|---|---|---|---|
| Gly | Gly Gln Asp Ile Ile Leu Tyr Trp Asp Ala Arg Gln Ala Pro Val | | |
| 290 | 295 | | 300 |

Gly Leu Ile Val Phe Ile Val Leu Ile Met Leu Val Val Gly Ala
305             310             315             320

Val Val Tyr Tyr Ile Trp Arg Arg Arg Ser Ala Tyr Gln Asp Ile Arg
                325             330             335

<210> SEQ ID NO 7
<211> LENGTH: 6486
<212> TYPE: DNA
<213> ORGANISM: Artificial Sequence
<220> FEATURE:
<223> OTHER INFORMATION: pLVsyn-CMV

<400> SEQUENCE: 7

```
tggaagggct aattcactcc caaagaagac aagatatcct tgatctgtgg atctaccaca      60
cacaaggcta cttccctgat tagcagaact acacaccagg gccagggstc agatatccac     120
tgacctttgg atggtgctac aagctagtac cagttgagcc agataaggta gaagaggcca     180
ataaaggaga gaacaccagc ttgttacacc ctgtgagcct gcatgggatg gatgacccgg     240
agagagaagt gttagagtgg aggtttgaca gccgcctagc atttcatcac gtggcccgag     300
agctgcatcc ggagtacttc aagaactgct gatatcgagc ttgctacaag gactttccg     360
ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata aagcttgcct     540
tgagtgcttc aagtagtgtg tgcccgtctg ttgtgtgact ctggtaacta gagatccctc     600
agaccctttt agtcagtgtg aaaatctct agcagtggcg cccgaacagg gacttgaaag     660
cgaaagggaa accagaggag ctctctcgac gcaggactcg gcttgctgaa gcgcgcacgg     720
caagaggcga ggggcggcga ctggtgagta cgccaaaaat tttgactagc ggaggctaga     780
aggagagaga tgggtgcgag agcgtcagta ttaagcgggg gagaattaga tcgcgatggg     840
aaaaaattcg gttaaggcca gggggaaaga aaaaatataa attaaaacat atagtatggg     900
caagcaggga gctagaacga ttcgcagtta atcctggcct gttagaaaca tcagaaggct     960
gtagacaaat actgggacag ctacaaccat cccttcagac aggatcagaa gaacttagat    1020
cattatataa tacagtagca accctctatt gtgtgcatca aaggatagag ataaaagaca    1080
ccaaggaagc tttagacaag atagaggaag agcaaaacaa aagtaagacc accgcacagc    1140
aagcggccgg ccgctgatct tcagacctgg aggaggagat gagggacaa attggagaag    1200
tgaattatat aaatataaag tagtaaaaat tgaaccatta ggagtagcac ccaccaaggc    1260
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg ggcatcaag cagctccagg caagaatcct    1500
ggctgtggaa agatacctaa aggatcaaca gctcctgggg atttggggtt gctctggaaa    1560
actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
```

-continued

```
tataaaatta ttcataatga tagtaggagg cttggtaggt ttaagaatag tttttgctgt    1860
actttctata gtgaatagag ttaggcaggg atattcacca ttatcgtttc agacccacct    1920
cccaaccccg aggggacccg acaggcccga aggaatagaa gaagaaggtg gagagagaga    1980
cagagacaga tccattcgat tagtgaacgg atctcgacgg tatcgccttt aaaagaaaag    2040
gggggattgg ggggtacagt gcaggggaaa gaatagtaga cataatagca acagacatac    2100
aaactaaaga attacaaaaa caaattacaa aaattcaaaa ttttcgggtt tattacaggg    2160
acagcagaga tccagtttat cgataagctt gggagttccg cgttacataa cttacggtaa    2220
atggcccgcc tggctgaccg cccaacgacc cccgcccatt gacgtcaata atgacgtatg    2280
ttcccatagt aacgccaata gggactttcc attgacgtca atgggtggag tatttacggt    2340
aaactgccca cttggcagta catcaagtgt atcatatgcc aagtacgccc cctattgacg    2400
tcaatgacgg taaatggccc gcctggcatt atgcccagta catgacctta tgggactttc    2460
ctacttggca gtacatctac gtattagtca tcgctattac catggtgatg cggttttggc    2520
agtacatcaa tgggcgtgga tagcggtttg actcacgggg atttccaagt ctccacccca    2580
ttgacgtcaa tgggagtttg ttttggcacc aaaatcaacg ggactttcca aaatgtcgta    2640
acaactccgc cccattgacg caaatgggcg gtaggcgtgt acggtgggag gtctatataa    2700
gcagagctcg tttagtgaac cgtcagatcg cctggagacg ccatccacgc tgttttgacc    2760
tccatagaag acaccgactc tactagagga tctatttccg gtgaattcct cgagactagt    2820
tctagagcgg ccgcggatcc acgcgtctgg aacaatcaac ctctggatta caaaatttgt    2880
gaaagattga ctggtattct taactatgtt gctcctttta cgctatgtgg atacgctgct    2940
ttaatgcctt tgtatcatgc tattgcttcc cgtatggctt tcattttctc ctccttgtat    3000
aaatcctggt tgctgtctct ttatgaggag ttgtggcccg ttgtcaggca acgtggcgtg    3060
gtgtgcactg tgtttgctga cgcaaccccc actggttggg gcattgccac cacctgtcag    3120
ctcctttccg ggactttcgc tttccccctc cctattgcca cggcggaact catcgccgcc    3180
tgccttgccc gctgctggac aggggctcgg ctgttgggca ctgacaattc cgtggtgttg    3240
tcggggaagc tgacgtcctt tccatggctg ctcgcctgtg ttgccacctg gattctgcgc    3300
gggacgtcct tctgctacgt cccttcggcc ctcaatccag cggaccttcc ttcccgcggc    3360
ctgctgccgg ctctgcggcc tcttccgcgt cttcgccttc gccctcagac gagtcggatc    3420
tccctttggg ccgcctcccc gcctggaatt aattctgcag tcgagaccta gaaaacatg    3480 gagcaatcac aagtagcaat acagcagcta ccaatgctga ttgtgcctgg ctagaagcac    3540
aagaggagga ggaggtgggt tttccagtca cacctcaggt acctttaaga ccaatgactt    3600
acaaggcagc tgtagatctt agccactttt taaaagaaaa gaggggactg aagggctaa    3660 ttcactccca acgaagacaa gatctgcttt ttgcttgtac tgggtctctc tggttagacc    3720
agatctgagc ctgggagctc tctggctaac tagggaaccc actgcttaag cctcaataaa    3780
gcttgccttg agtgcttcaa gtagtgtgtg cccgtctgtt gtgtgactct ggtaactaga    3840
gatccctcag acccttttag tcagtgtgga aatctctag cagtagtagt tcatgtcatc    3900
ttattattca gtatttataa cttgcaaaga atgaatatc agagagtgag aggccttgac    3960
attgctagcg ttttaccgtc gacctctagc tagagcttgg cgtaatcatg gtcatagctg    4020
tttcctgtgt gaaattgtta tccgctcaca attccacaca acatacgagc cggaagcata    4080
aagtgtaaag cctggggtgc ctaatgagtg agctaactca cattaattgc gttgcgctca    4140
```

-continued

```
ctgcccgctt tccagtcggg aaacctgtcg tgccagctgc attaatgaat cggccaacgc   4200
gcggggagag gcggtttgcg tattgggcgc tcttccgctt cctcgctcac tgactcgctg   4260
cgctcggtcg ttcggctgcg gcgagcggta tcagctcact caaaggcggt aatacggtta   4320
tccacagaat caggggataa cgcaggaaag aacatgtgag caaaaggcca gcaaaaggcc   4380
aggaaccgta aaaaggccgc gttgctggcg ttttccata ggctccgccc ccctgacgag   4440
catcacaaaa atcgacgctc aagtcagagg tggcgaaacc cgacaggact ataaagatac   4500
caggcgtttc ccctggaag ctccctcgtg cgctctcctg ttccgaccct gccgcttacc   4560
ggatacctgt ccgcctttct cccttcggga agcgtggcgc tttctcatag ctcacgctgt   4620
aggtatctca gttcggtgta ggtcgttcgc tccaagctgg gctgtgtgca cgaaccccc   4680 gttcagcccg accgctgcgc cttatccggt aactatcgtc ttgagtccaa cccggtaaga   4740
cacgacttat cgccactggc agcagccact ggtaacagga ttagcagagc gaggtatgta   4800
ggcggtgcta cagagttctt gaagtggtgg cctaactacg gctacactag aagaacagta   4860
tttggtatct gcgctctgct gaagccagtt accttcggaa aaagagttgg tagctcttga   4920
tccggcaaac aaaccaccgc tggtagcggt ggtttttttg tttgcaagca gcagattacg   4980
cgcagaaaaa aaggatctca agaagatcct ttgatctttt ctacgggtc tgacgctcag   5040 tggaacgaaa actcacgtta agggattttg gtcatgagat tatcaaaaag gatcttcacc   5100
tagatccttt taaattaaaa atgaagtttt aaatcaatct aaagtatata tgagtaaact   5160
tggtctgaca gttaccaatg cttaatcagt gaggcaccta tctcagcgat ctgtctattt   5220
cgttcatcca tagttgcctg actccccgtc gtgtagataa ctacgatacg ggagggctta   5280
ccatctggcc ccagtgctgc aatgatacg cgagaccca gctcaccggc tccagattta   5340
tcagcaataa accagccagc cggaagggcc gagcgcagaa gtggtcctgc aactttatcc   5400
gcctccatcc agtctattaa ttgttgccgg gaagctagag taagtagttc gccagttaat   5460
agtttgcgca acgttgttgc cattgctaca ggcatcgtgg tgtcacgctc gtcgtttggt   5520
atggcttcat tcagctccgg ttcccaacga tcaaggcgag ttacatgatc ccccatgttg   5580
tgcaaaaaag cggttagctc cttcggtcct ccgatcgttg tcagaagtaa gttggccgca   5640
gtgttatcac tcatggttat ggcagcactg cataattctc ttactgtcat gccatccgta   5700
agatgctttt ctgtgactgg tgagtactca accaagtcat tctgagaata gtgtatgcgg   5760
cgaccgagtt gctcttgccc ggcgtcaata cgggataata ccgcgccaca tagcagaact   5820
ttaaaagtgc tcatcattgg aaaacgttct tcggggcgaa aactctcaag gatcttaccg   5880
ctgttgagat ccagttcgat gtaacccact cgtgcaccca actgatcttc agcatctttt   5940
actttcacca gcgtttctgg gtgagcaaaa acaggaaggc aaaatgccgc aaaaaaggga   6000
ataagggcga cacggaaatg ttgaatactc atactcttcc ttttcaata ttattgaagc   6060 atttatcagg gttattgtct catgagcgga tacatatttg aatgtattta gaaaaataaa   6120 caaataggg ttccgcgcac atttccccga aaagtgccac ctgacgtcga cggatcggga   6180
gatcaacttg tttattgcag cttataatgg ttacaaataa agcaatagca tcacaaattt   6240
cacaaataaa gcattttttt cactgcattc tagttgtggt ttgtccaaac tcatcaatgt   6300
atcttatcat gtctggatca actggataac tcaagctaac caaaatcatc ccaaacttcc   6360 cacccccatac cctattacca ctgccaatta cctgtggttt catttactct aaacctgtga   6420
```

```
ttcctctgaa ttattttcat tttaaagaaa ttgtatttgt taaatatgta ctacaaactt    6480
agtagt                                                               6486
```